(12) United States Patent
Chen et al.

(10) Patent No.: US 6,486,379 B1
(45) Date of Patent: Nov. 26, 2002

(54) ABSORBENT ARTICLE WITH CENTRAL PLEDGET AND DEFORMATION CONTROL

(75) Inventors: Fung-jou Chen, Appleton, WI (US); Jeffrey Dean Lindsay, Appleton, WI (US); Julie Marie Bednarz, Neenah, WI (US); Joseph DiPalma, Neenah, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 0 days.

(21) Appl. No.: 09/408,498

(22) Filed: Oct. 1, 1999

(51) Int. Cl.[7] ............................................. A61F 13/15

(52) U.S. Cl. ........................................ 604/378; 604/379
(58) Field of Search ................................ 604/378, 379, 604/380, 385.01, 385.101

(56) References Cited

U.S. PATENT DOCUMENTS

| | | |
|---|---|---|
| 2,064,431 A | 12/1936 | Jurgensen |
| 2,683,457 A | 7/1954 | Cunningham |
| 2,747,575 A | 5/1956 | Mercer |
| 3,126,888 A | 3/1964 | Woldman |
| 3,156,242 A | 11/1964 | Crowe, Jr. |
| 3,294,091 A | 12/1966 | Morse |
| 3,575,174 A | 4/1971 | Mogor |
| 3,667,466 A | 6/1972 | Ralph |
| 3,860,003 A | 1/1975 | Buell |
| 3,881,489 A | 5/1975 | Hartwell |
| 3,881,491 A | 5/1975 | Whyte |
| 3,921,232 A | 11/1975 | Whyte |
| 3,989,867 A | 11/1976 | Sisson |
| 4,015,604 A | 4/1977 | Csillag |
| 4,100,324 A | 7/1978 | Anderson et al. |
| 4,195,634 A | 4/1980 | DiSalvo et al. |
| 4,247,362 A | 1/1981 | Williams |
| 4,285,343 A | 8/1981 | McNair |
| 4,324,246 A | 4/1982 | Mullane et al. |
| 4,342,314 A | 8/1982 | Radel et al. |
| 4,397,644 A | 8/1983 | Matthews et al. |
| 4,405,326 A | 9/1983 | Lenaghan |
| 4,421,812 A | 12/1983 | Plant |
| 4,425,130 A | 1/1984 | DesMarais |
| 4,463,045 A | 7/1984 | Ahr et al. |
| 4,476,180 A | 10/1984 | Wnuk |

(List continued on next page.)

FOREIGN PATENT DOCUMENTS

| | | |
|---|---|---|
| AU | 699325 | 12/1998 |
| CA | 884608 | 11/1971 |
| DE | 196 40 451 A1 | 4/1998 |

(List continued on next page.)

OTHER PUBLICATIONS

AATCC Test Method 127–1977, "Water Resistance: Hydrostatic Pressure Test," Technical Manual of the American Association of Textile Chemists and Colorists, reaffirmed 1977, p. 242.

(List continued on next page.)

*Primary Examiner*—Aaron J. Lewis
*Assistant Examiner*—Michele Kidwell
(74) *Attorney, Agent, or Firm*—Pauley Petersen Kinne & Erickson

(57) ABSTRACT

An absorbent article is disclosed having excellent body fit, center-fill fluid handling performance, and good leakage control in that flow from the center of the article to the longitudinal sides thereof is hindered by a wicking barrier. The article comprises a lower absorbent member, an horizontal wicking barrier over the lower absorbent member, and a central absorbent section forming a medial hump over the horizontal wicking barrier. An optional central rising member can further enhance the topography of the article when compressed by urging a central portion to deflect vertically upward. In one embodiment, longitudinal upward projections on the horizontal wicking barrier also help control the deformation of the article for good body fit.

37 Claims, 9 Drawing Sheets

U.S. PATENT DOCUMENTS

| | | |
|---|---|---|
| 4,480,516 A | 11/1984 | Leroy |
| 4,490,147 A | 12/1984 | Pierce et al. |
| 4,496,359 A | 1/1985 | Pigneul |
| 4,536,181 A | 8/1985 | Cook |
| 4,556,146 A | 12/1985 | Swanson et al. |
| 4,556,560 A | 12/1985 | Buckingham |
| 4,573,986 A | 3/1986 | Minetola et al. |
| 4,576,596 A | 3/1986 | Jackson et al. |
| 4,576,597 A | 3/1986 | Hlaban et al. |
| 4,578,070 A | 3/1986 | Holtman |
| 4,589,876 A | 5/1986 | Van Tilburg |
| 4,608,047 A | 8/1986 | Mattingly |
| 4,654,040 A | 3/1987 | Luceri |
| 4,655,759 A | 4/1987 | Romans-Hess et al. |
| 4,662,876 A | 5/1987 | Wiegner |
| 4,687,478 A | 8/1987 | Van Tilburg |
| 4,701,177 A | 10/1987 | Ellis et al. |
| RE32,649 E | 4/1988 | Brandt et al. |
| 4,738,677 A | 4/1988 | Foreman |
| 4,753,644 A | 6/1988 | Cottenden et al. |
| 4,758,240 A | 7/1988 | Glassman |
| 4,804,380 A | 2/1989 | Lassen et al. |
| 4,846,824 A | 7/1989 | Lassen et al. |
| 4,879,170 A | 11/1989 | Radwanski et al. |
| 4,886,513 A | 12/1989 | Mason, Jr. et al. |
| 4,936,839 A | 6/1990 | Molee et al. |
| 4,950,264 A | 8/1990 | Osborn, III |
| 4,961,736 A | 10/1990 | McCloud |
| 4,964,857 A | 10/1990 | Osborn |
| 4,973,325 A | 11/1990 | Sherrod et al. |
| 5,007,906 A | 4/1991 | Osborn, III et al. |
| 5,009,653 A | 4/1991 | Osborn, III |
| 5,030,314 A | 7/1991 | Lang |
| 5,147,343 A | 9/1992 | Kellenberger |
| 5,147,345 A | 9/1992 | Young et al. |
| 5,151,092 A | 9/1992 | Buell et al. |
| 5,188,625 A | 2/1993 | Van Iten et al. |
| 5,217,445 A | 6/1993 | Young et al. |
| 5,217,447 A | 6/1993 | Gagnon |
| 5,219,342 A | 6/1993 | Hatch et al. |
| 5,235,515 A | 8/1993 | Ungpiyakul et al. |
| 5,236,428 A | 8/1993 | Zajaczkowski |
| 5,267,992 A | 12/1993 | Van Tilburg |
| 5,300,055 A | 4/1994 | Buell |
| 5,308,346 A | 5/1994 | Sneller et al. |
| 5,324,278 A * | 6/1994 | Visscher et al. ........ 604/385.01 |
| 5,324,575 A | 6/1994 | Sultze et al. |
| 5,342,337 A | 8/1994 | Runeman et al. |
| 5,342,342 A | 8/1994 | Kitaoka |
| 5,350,624 A | 9/1994 | Georger et al. |
| 5,354,400 A | 10/1994 | Lavash et al. |
| 5,360,420 A | 11/1994 | Cook et al. |
| 5,389,094 A | 2/1995 | Lavash et al. |
| 5,399,175 A | 3/1995 | Glaug et al. |
| 5,399,412 A | 3/1995 | Sudall et al. |
| 5,401,267 A | 3/1995 | Couture-Dorschner et al. |
| 5,413,568 A | 5/1995 | Roach et al. |
| 5,415,643 A | 5/1995 | Kolb |
| 5,429,628 A | 7/1995 | Trinh et al. |
| 5,429,629 A | 7/1995 | Latimer et al. |
| 5,429,630 A | 7/1995 | Beal et al. |
| 5,445,628 A | 8/1995 | Gipson et al. |
| 5,447,507 A | 9/1995 | Yamamoto |
| 5,462,166 A | 10/1995 | Minton et al. |
| 5,476,457 A | 12/1995 | Roessler et al. |
| 5,487,736 A | 1/1996 | Van Phan |
| 5,489,283 A | 2/1996 | Van Tillburg |
| 5,506,035 A | 4/1996 | Van Phan et al. |
| 5,514,104 A | 5/1996 | Cole et al. |
| 5,518,801 A | 5/1996 | Chappell et al. |
| 5,520,674 A | 5/1996 | Lavon et al. |
| 5,533,991 A | 7/1996 | Kirby et al. |
| 5,542,941 A | 8/1996 | Morita |
| 5,545,156 A | 8/1996 | DiPalma et al. |
| 5,547,745 A | 8/1996 | Hansen et al. |
| 5,562,645 A | 10/1996 | Tanzer et al. |
| 5,562,650 A | 10/1996 | Everett et al. |
| 5,567,260 A | 10/1996 | McFall |
| 5,575,785 A | 11/1996 | Gryskiewicz et al. |
| 5,591,146 A | 1/1997 | Hasse |
| 5,591,148 A * | 1/1997 | McFall et al. .............. 604/378 |
| 5,591,150 A | 1/1997 | Olsen et al. |
| 5,599,339 A | 2/1997 | Horney |
| 5,601,544 A | 2/1997 | Glaug et al. |
| 5,611,790 A | 3/1997 | Osborn, III et al. |
| 5,618,282 A | 4/1997 | Schlangen |
| 5,620,430 A | 4/1997 | Bamber |
| 5,624,423 A | 4/1997 | Anjur et al. |
| 5,649,917 A | 7/1997 | Roberts et al. |
| 5,672,248 A | 9/1997 | Wendt et al. |
| 5,692,939 A | 12/1997 | DesMarais |
| 5,693,411 A | 12/1997 | Hansen et al. |
| 5,702,378 A | 12/1997 | Widlund et al. |
| 5,704,928 A | 1/1998 | Morita et al. |
| 5,704,930 A | 1/1998 | Lavash et al. |
| 5,704,932 A | 1/1998 | Hibbard |
| 5,711,970 A | 1/1998 | Lau et al. |
| 5,720,738 A | 2/1998 | Clark |
| 5,725,821 A | 3/1998 | Gannon et al. |
| 5,746,729 A | 5/1998 | Wada et al. |
| 5,753,343 A | 5/1998 | Braun et al. |
| 5,766,213 A | 6/1998 | Hackman et al. |
| 5,769,834 A | 6/1998 | Reiter et al. |
| 5,772,967 A | 6/1998 | Wannlund et al. |
| 5,773,120 A | 6/1998 | Deka et al. |
| 5,779,860 A | 7/1998 | Hollenberg et al. |
| 5,795,921 A | 8/1998 | Dyer et al. |
| 5,800,417 A | 9/1998 | Goerg-Wood et al. |
| 5,817,079 A | 10/1998 | Bergquist et al. |
| 5,817,081 A | 10/1998 | LaVon et al. |
| 5,817,394 A | 10/1998 | Alikhan et al. |
| 5,820,616 A | 10/1998 | Horney |
| 5,824,004 A | 10/1998 | Osborn, III et al. |
| 5,846,230 A | 12/1998 | Osborn, III et al. |
| 5,851,648 A | 12/1998 | Stone et al. |
| 5,853,867 A | 12/1998 | Harada et al. |
| 5,858,011 A | 1/1999 | Brown et al. |
| 5,858,021 A | 1/1999 | Sun et al. |
| 5,865,824 A | 2/1999 | Chen et al. |
| 5,869,033 A | 2/1999 | Schulz |
| 5,874,070 A | 2/1999 | Trinh et al. |
| 5,874,071 A | 2/1999 | Yu et al. |
| 5,876,393 A | 3/1999 | Ahr et al. |
| 5,910,137 A | 6/1999 | Clark et al. |
| 5,954,705 A | 9/1999 | Sawaki et al. |
| 5,957,909 A * | 9/1999 | Hammons et al. .......... 604/387 |
| 5,990,377 A | 11/1999 | Chen et al. |

FOREIGN PATENT DOCUMENTS

| | | |
|---|---|---|
| EP | 0 136 524 | 4/1985 |
| EP | 0 360 285 | 3/1990 |
| EP | 0 400 895 A1 | 12/1990 |
| EP | 0 520 884 | 12/1992 |
| EP | 0 117 613 B2 | 3/1993 |
| EP | 0 564 307 A1 | 10/1993 |
| EP | 0 687 453 | 12/1995 |
| EP | 0 612 233 B1 | 4/1996 |
| EP | 0 552 345 B1 | 9/1996 |
| EP | 0 516 964 B1 | 11/1996 |
| EP | 0 758 543 | 2/1997 |
| EP | 0 768 070 | 4/1997 |

| | | | |
|---|---|---|---|
| EP | 0 638 303 B1 | 11/1997 | |
| EP | 0 804 914 | 11/1997 | |
| EP | 0 815 817 | 1/1998 | |
| EP | 0 652 736 B1 | 10/1998 | |
| EP | 0 868 894 | 10/1998 | |
| EP | 0 419 434 B2 | 11/1998 | |
| EP | 0 758 220 B1 | 12/1998 | |
| EP | 0 893 517 A2 | 1/1999 | |
| EP | 0 945 110 | 9/1999 | |
| GB | 2 168 612 | 12/1984 | |
| GB | 2 306 333 | 10/1996 | |
| WO | WO 83/03051 A1 | 9/1983 | |
| WO | WO 92/07535 A1 | 5/1992 | |
| WO | WO 93/21879 A1 | 11/1993 | |
| WO | 94/24973 | 11/1994 | |
| WO | WO 95/24878 A1 | 9/1995 | |
| WO | WO 97/19808 A1 | 6/1997 | |
| WO | WO 97/24283 A1 | 7/1997 | |
| WO | WO 97/34557 | * 9/1997 | ........... A61F/13/15 |
| WO | WO 97/34558 | * 9/1997 | ........... A61F/13/15 |
| WO | WO 98/22059 A1 | 5/1998 | |
| WO | WO 98/24391 A2 | 6/1998 | |
| WO | WO 98/43684 A1 | 10/1998 | |
| WO | WO 99/00093 A1 | 1/1999 | |
| WO | 99/12502 | 3/1999 | |
| WO | 00/19955 | 4/2000 | |
| WO | 00/19956 | 4/2000 | |
| ZA | 98/4033 | 5/1998 | |

OTHER PUBLICATIONS

American Society for Testing Materials (ASTM) Designation: D 3574–91, "Standard Test Methods for Flexible Cellular Materials—Slab, Bonded, and Molded Urethane Foams," pp. 303–319, published Mar. 1992.

American Society for Testing Materials (ASTM) Designation: D 4032–82, "Standard Test Method for Stiffness of Fabric by the Circular Bend Procedure," pp. 702–706 published Aug. 1982.

Federal Specification UU–T–595b, "Towel, Wiping, Paper: Industrial And Institutional," Apr. 4, 1967, 8 pages.

Federal Specification UU–T–595c, "Towel, Wiping, Paper: Industrial And Institutional," Jul. 27, 1976, 8 pages.

Gibson, P.W. et al., "Electrospun Fiber Mats: Transport Properties," AIChE Journal, vol. 45, No. 1, Jan. 1999, pp. 190–195.

Kim, S.H. et al., "Synthesis and Characterization of Dextran–Based Hydrogel Prepared By Photocrosslinking," Carbohydrate Polymers, vol. 40, No. 3, Sep. 1999, pp. 183–190.

Krema, Radko et al., "What's New In Highloft Production?" Nonwovens Industry, Oct. 1997, pp. 74–78.

Lee, Seungsin et al., "Antimicrobial and Blood Repellent Finishes for Cotton and Nonwoven Fabrics Based on Chitosan and Fluoropolymers," Textile Research Journal, 69(2), Feb. 1999, pp. 104–112.

Rahn, K. et al., "New Cellulosic Polymers By Subsequent Modification of 2,3–Dialdehyde Cellulose," Cellulose Chemistry and Technology, 32, 1998, pp. 173–183.

* cited by examiner

ABSORBENT ARTICLE WITH CENTRAL PLEDGET AND DEFORMATION CONTROL

BACKGROUND OF THE INVENTION

To prevent leakage of body exudates from absorbent articles such as feminine care pads or napkins and disposable diapers, it is desirable that the exudates not reach the edges of the absorbent material in the article. A "center fill" strategy is desirable for leakage control, wherein fluids are preferentially held in a central region of the article. Unfortunately, in traditional absorbent articles, there is generally no barrier to bulk flow or capillary wicking from the target region (the place where intake of fluids occurs) to the edges of the article, so leaking from the edges of the article is a persistent problem. Thus, in traditional articles, fluid entering the center of the article still has the potential to travel through absorbent material directly to the sides and leak. Flow from the center to the sides can be especially rapid when the article is compressed, bringing the wet central portion of the article in contact with absorbent material at the sides of the article.

The ability of an absorbent article to promote center fill and reduce leakage depends on the goodness of body fit achieved by the article in use. In sanitary napkins and other absorbent articles, the article as worn is often compressed laterally by the legs of the wearer, causing significant deformation of the article. In many conventional articles, the deformation is random or uncontrolled, resulting in a variety of product configurations that often may be inadequate for good uptake and fluid distribution in the article.

Past efforts to improve body fit and promote liquid uptake in the center of the article have included three-dimensional structures with central humps or elevated central members resting above the plane of a flat absorbent core. The elevated member can be a cylinder or an inverted U-shaped tube, for example. However, the article with an elevated central member can still suffer from leakage and smearing from fluid leaving the sides of the member. Further, deformation of the entire article may be poorly controlled, resulting in poor body fit in many cases even with a central elevated region.

What is needed is an absorbent article with internal barriers to prevent leakage to the sides and offering good control of the deformation of the absorbent material when worn such that absorbent material is placed close to the source of body exudates. What is needed further is a thin absorbent article with good center fill performance that can reduce leakage and offer excellent body fit through the efficient use of a small amount of absorbent material while maintaining comfort.

SUMMARY OF THE INVENTION

It has been discovered that a layered absorbent core with a horizontal wicking barrier between two superposed layers provides opportunities for improved leakage prevention, better body fit, and more efficient use of the absorbent material of the core if certain design principles are followed to promote the upward deflection of the central portion of the absorbent core toward the body of the wearer. The design principles require that the absorbent core be divided into two parts, a lower absorbent member and a central absorbent section, with a horizontal wicking barrier separating the two parts to reduce the tendency for fluid to flow through the absorbent material from the central target region of the article toward the longitudinal sides of the article.

Hence, in one aspect, the invention resides in an absorbent article for use on the body of a wearer, the absorbent article having a longitudinal centerline, a transverse centerline, two longitudinal sides, a target zone and a body side, the absorbent article comprising:

a) a liquid impervious backsheet;
b) a liquid pervious topsheet attached to the backsheet;
c) a lower absorbent member disposed above the backsheet, the lower absorbent member comprising a pair of spaced apart, substantially longitudinal crease lines in the target zone disposed on opposite sides of the longitudinal centerline of the article, the pair of crease lines having a distance therebetween;
d) a horizontal wicking barrier disposed above the lower absorbent member;
e) a middle absorbent member having a width less than the distance between the crease lines in the target zone, the middle absorbent member being disposed above the horizontal wicking barrier; and
f) an upper absorbent member having longitudinal sides and a width in the target zone greater than the width of the middle absorbent member and less than the width of the horizontal wicking barrier, disposed above the middle absorbent member and beneath the topsheet.

In another aspect, the invention resides in an absorbent article having a target zone, the absorbent article comprising:

a) a liquid impervious backsheet;
b) a lower absorbent member disposed above the backsheet;
c) a horizontal wicking barrier disposed over the lower absorbent member, the wicking barrier having a width in the target zone;
d) a middle absorbent member disposed above the wicking barrier and having a maximum width in the target zone;
e) an upper absorbent member disposed above the middle absorbent member having a width in the target zone no less than the maximum width of the middle absorbent member in the target zone, the upper absorbent member being predisposed to deflect upward during laterally inward compression of the absorbent article; and
f) a topsheet connected to the backsheet.

In another aspect, the invention resides in an absorbent article having a target zone, a longitudinal direction, a transverse direction, a vertical direction substantially normal to both the longitudinal and transverse directions, and a body side, the absorbent article comprising:

a) a liquid impervious backsheet;
b) a lower absorbent member disposed above the backsheet;
c) a horizontal wicking barrier disposed over the lower absorbent member, the horizontal wicking barrier having a width in the target zone;
d) a pre-shaped upper absorbent member disposed above the horizontal wicking barrier, the pre-shaped upper absorbent member being shaped to define a medial hump therein and to define a voidspace between the horizontal wicking barrier and the medial hump, the pre-shaped upper absorbent member having a width in the target zone no greater than the width in the target zone of the horizontal wicking barrier; and
e) a topsheet disposed above the pre-shaped upper absorbent member and attached to the backsheet.

The voidspace of the above article can optionally but desirably be filled in part with a middle absorbent member including loose fibrous material such as hardwood nits, absorbent particulates, high-bulk fluff pulp, tissue layers, and the like. Generally, the pre-shaped upper absorbent member is geometrically predisposed to flex upward during laterally inward compression.

In another aspect, the invention resides in a method for producing an absorbent article having a longitudinal centerline and a transverse centerline substantially normal to the longitudinal centerline comprising:

a) providing a backsheet;

b) disposing a substantially planar lower absorbent member above the backsheet, the lower absorbent member having a width along the transverse centerline of the article and comprising longitudinal crease lines therein;

c) disposing a horizontal wicking barrier over the lower absorbent member;

d) disposing a middle absorbent member over the horizontal wicking barrier, the middle absorbent member being substantially centered about the longitudinal centerline of the article and having a width substantially less than the width of the lower absorbent member along the transverse centerline of the article;

e) disposing an upper absorbent member over the middle absorbent member, the upper absorbent member having a width along the transverse centerline of the article greater than the width of the middle absorbent member;

f) disposing a topsheet above the upper absorbent member and the lower absorbent member; and g) securing the topsheet to the backsheet.

In still another aspect, the invention resides in a method for producing an absorbent article having a target zone, comprising:

a) providing a liquid impervious backsheet;

b) disposing a lower absorbent member above the backsheet;

c) disposing a horizontal wicking barrier over the lower absorbent member, the wicking barrier having a width in the target zone;

d) pre-shaping an upper absorbent member to form a pre-shaped upper absorbent member having a medial hump therein, such that a voidspace is defined beneath the medial hump when the pre-shaped upper absorbent member rests on a flat surface with the medial hump placed away from the flat surface;

e) disposing the pre-shaped upper absorbent member above the horizontal wicking barrier with the medial hump away from the horizontal wicking barrier; and f) disposing a topsheet over the pre-shaped upper absorbent member;

g) and attaching the topsheet to the backsheet.

The absorbent members of the core can be fluff pulp, airlaid webs, multiple layers of tissue, coform, absorbent foams, and the like. The central absorbent section of the absorbent core is above the horizontal wicking barrier and comprises at least two layers, a middle absorbent member preferably centrally located in the absorbent article, and an upper absorbent member that is wider than the middle absorbent member. Desirably, the middle absorbent member is substantially thicker than the upper absorbent member. The upper absorbent member conforms at least in part to the shape of the smaller middle absorbent member such that a medial hump is formed in the absorbent core for improved body fit.

The lower absorbent member desirably provides shaping to control the deformation and fit of the pad and provides additional absorbent capacity in case the central absorbent section cannot retain all of the fluid received. The lower absorbent member may be a single contiguous piece, or may comprise a plurality of discrete sections or layers. The lower absorbent member can be provided with a central void beneath the horizontal wicking barrier to reduce the amount of material in the absorbent article since the central portion of the lower absorbent member may not be needed for fluid retention.

Desirably, the topography of the absorbent article is further enhanced in the target zone by laterally inward compression when worn, giving rise to a substantially W-shaped article in the target zone. Crease lines such as embossments or slits in the lower absorbent member and/or the upper absorbent member promote predominantly longitudinal valley folds in the absorbent core away from the longitudinal centerline. The crease lines help enable the desired deformation of the outer portions of the absorbent core to achieve good body fit, while the medial hump and other central elements help promote upward deflection of absorbent core, also for improved body fit. Thus, there is a positive interaction between the medial hump and the crease lines in the absorbent core that promotes good body fit.

In addition to crease lines to promote downward folding of the article, shaping can also be directed by shaping lines that promote upward folding (e.g., a mountain fold) during lateral compression from the longitudinal sides of the article. A shaping line, if present, should be in the central absorbent section of the article. A shaping line near the longitudinal centerline coupled with two crease lines away from the longitudinal centerline can interact during lateral compression to establish a W-fold geometry in the article.

The entire absorbent core together desirably is soft and flexible to readily conform to the body and to permit deformation of components therein to flex toward the body when the article is worn.

In a preferred embodiment, the good body fit and leakage control capabilities of the present invention derive in part from upward deflection of substantially the entire absorbent core in the central portion of the target zone, meaning that the lower absorbent member and the upper absorbent member are both deflected toward the body, rather than the upper absorbent member alone deflecting toward the body or some other member above the absorbent core deflecting toward the body without the lower absorbent member also deflecting toward the body.

The horizontal wicking barrier plays an important role in promoting center fill and preventing leakage of fluids. The horizontal wicking barrier spans a horizontal distance (even though it may not rest in a single horizontal plane) on the surface of the lower absorbent member beyond the periphery of the upper absorbent member, particularly in the target zone. Thus, the horizontal wicking barrier in the target zone is wider than either of the middle absorbent member and the upper absorbent member to hinder wicking contact between the central absorbent section and the lower absorbent member.

The portion of horizontal wicking barrier on the surface of the lower absorbent member and outside the periphery of the upper absorbent member is the "ledge" or "exposed portion of the horizontal wicking barrier." The ledge helps prevent wicking contact between the central absorbent section and the adjacent lower absorbent member, even when the article is laterally compressed. It can also redirect flow toward the central absorbent section and enhance the center-fill effect.

When fluid is deposited on such a ledge, the fluid can be redirected toward the central absorbent section instead of flowing into the underlying lower absorbent member. In a related embodiment, the ledge can substantially cover all of the body side surface of the lower absorbent member outside the perimeter of the central absorbent section. Thus, the ledge can provide wicking isolation of the central absorbent section from the lower absorbent member even under extreme bunching of the article during dynamic use.

The horizontal wicking barrier is preferably a thin, flexible web or film that does not wick fluid or at least wicks fluid significantly more slowly than the absorbent material of the core. The horizontal wicking barrier desirably is a hydrophobic polyolefin film or web, such as a polyethylene film or a meltblown web. In a preferred embodiment, the wicking barrier is impervious to liquid except where optional apertures have been provided to permit a limited degree of flow from the central absorbent section to underlying portions of the lower absorbent member. Less preferably, the wicking barrier can also comprise in part hydrophobic matter that is used to impregnate or coat a portion of the lower absorbent member to reduce lateral wicking by providing a substantially impervious zone in the lower absorbent member. Such hydrophobic matter can include adhesives and particularly hot melt adhesives added to the absorbent article while molten; wax; silicone-based materials; polyolefins and the like.

The horizontal wicking barrier can be a smooth film with relatively low friction, permitting sliding or motion of portions of the middle absorbent member relative to the horizontal wicking barrier when the article is laterally compressed to improve body fit.

Good body fit can be further promoted by a central rising member disposed in or beneath the absorbent core. The central rising member, described more fully hereafter, deflects upward upon lateral compression from the longitudinal sides of the article. The deflection of the central rising member in turns deflects the upper absorbent member toward the body of the wearer.

The optional central rising member can be any of a variety of structures which deflect upward when laterally compressed from the longitudinal sides, including an absorbent web folded into the shape of the letter "e" prior to flattening, with a centerline aligned with the longitudinal centerline of the article (the flat cross-bar of the "e"-shape lying in the transverse direction, normal to the longitudinal centerline of the article). Upon lateral compression from the longitudinal sides of the article, the flattened "e" shape deflects upwardly, the upper loop of the "e" shape springing back into the approximate shape of a semicircle to urge the upper surface of the upper absorbent member toward the body of the wearer. Collapsed tubes and other structures disclosed below can also serve as a central rising member.

The central rising member can comprise a thermoplastic deformation element as disclosed by K. B. Buell in U.S. Pat. No. 5,300,055, issued Apr. 5, 1994, but the central rising member can also be non-thermoplastic such as a densified cellulosic web. Thus, the central rising member can have a flexure means, and particularly a longitudinally extending flexure hinge, for inducing the body facing surface of the central rising member to have a convex upward configuration when the sanitary napkin is worn.

Many embodiments of the present invention are intended to be worn in the crotch of a wearer, and thus have crotch regions. However, the present invention can also be applied to other articles such as wound dressings where a crotch region may not exist. In such cases, the article will have a region where fluid intake is intended to occur, termed the "target region." The portion of the article including the longitudinal length of the target region and the full transverse width of the article normal to length of the target region is defined herein as the "target zone." For articles intended to be worn in the crotch, the terms "target zone" and "crotch region" are generally synonymous, whereas "target region" generally excludes the portions of the absorbent core near the longitudinal sides since the intended area for fluid intake is generally substantially central to the absorbent article.

Possible uses of the present invention include absorbent articles for intake, distribution, and retention of human body fluids, such as feminine care pads and related catamenial devices or sanitary napkins, including "ultra-thin" pads, pantiliners and maxipads. Likewise, the present invention can be applied to diapers, disposable training pants, other disposable garments such as swimming garments, incontinence articles, bed pads, bandages, or other absorbent articles. The present invention can also be incorporated in articles adapted for particular portions of garments to be worn on the human body, ostomy bags, and medical absorbents and wound dressings. The articles of the present invention provide significant leakage protection, fluid center-fill absorptive performance, and other desirable attributes for absorbent articles.

Preferably, the pre-shaped upper absorbent member is an airlaid web comprising cellulosic fibers and a binder such as a thermoplastic binder material, a heat-setting resin, or a heat-activated crosslinking agent, wherein the medial hump is formed by thermal molding of the airlaid web, exemplified by using mechanical or pneumatic pressure to deform an airlaid web against a molding surface, followed by application of heat to activate the binder and stabilize the airlaid web so it maintains its shape after removal from the molding surface.

For feminine care pads in particular, the present invention offers surprising advantages in terms of comfort and fit. In sanitary napkins, the upward mound that is created near the longitudinal centerline of the article by the upward motion of the central regions of the absorbent article as directed by shaping lines, does not persist throughout the length of the article, but, as influenced by the shaping lines, terminates just outside the crotch region to permit the article to better conform to the regions outside the crotch area, where an inverted V-shape may be useful in the rear of the article to better conform to the buttocks, and where the article generally should be relatively flat in the transverse direction and curled concave up in the longitudinal direction for best body fit in the front of the pad. Proper shaping of regions outside the crotch region during lateral compression can be achieved by providing additional slits, reinforcing elements, elastic components, or attachment elements to the absorbent core.

DEFINITIONS

As used herein, a material is said to be "absorbent" if it can retain an amount of water equal to at least 100% of its dry weight as measured by the test for Intrinsic Absorbent Capacity given below (i.e., the material has an Intrinsic Absorbent Capacity of at about 1 or greater). Desirably, the absorbent materials used in the absorbent members of the present invention have an Intrinsic Absorbent Capacity of about 2 or greater, more specifically about 4 or greater, more specifically still about 7 or greater, and more specifically still about 10 or greater, with exemplary ranges of from about 4 to about 25 or from about 12 to about 40.

As used herein, the term "absorbent article" refers to devices which absorb and contain liquids such as body exudates, and, more specifically, refers to devices which are placed against or in proximity to the body of the wearer to absorb and contain the various exudates discharged from the body.

As used herein, "absorbent capacity" refers to the total mass of water that a specified quantity of absorbent material can hold, and is simply the Intrinsic Absorbent Capacity (described hereafter) multiplied by the dry mass of the absorbent material. Thus 10 g of material having an Intrinsic Absorbent Capacity of 5 has an absorbent capacity of 50 g (or about 50 ml of fluid).

As used herein, "bulk" and "density," unless otherwise specified, are based on an oven-dry mass of a sample and a thickness measurement made at a load of 0.34 kPa (0.05 psi) with a 7.62-cm (three-inch) diameter circular platen. Thickness measurements of samples are made in a TAPPI-conditioned room (50% relative humidity, 23° C.) after conditioning for at least four hours. Samples should be flat and uniform under the area of the contacting platen. Bulk is expressed as cc/g and density is the inverse, g/cc.

As used herein, the term "cellulosic" is meant to include any material having cellulose as a major constituent, and specifically comprising at least 50 percent by weight cellulose or a cellulose derivative. Thus, the term includes cotton, typical wood pulps, nonwoody cellulosic fibers, cellulose acetate, cellulose triacetate, rayon, thermomechanical wood pulp, chemical wood pulp, debonded chemical wood pulp, milkweed, or bacterial cellulose.

As used herein, "Central Elevation" is defined as the height difference between the center of the upper absorbent member along the transverse centerline of the article and the average height of the longitudinal sides of the upper absorbent member along the transverse centerline of the article at the end of the Vertical Deformation Test as described hereinafter. The Central Elevation for absorbent articles of the present invention can be at least about 0.5 cm, specifically at least about 1 cm, and more specifically at least about 1.2 cm and up to about 10 cm. Desirably, an absorbent article of the present invention exhibits an increase in Central Elevation in the crotch region of at least about 20%, and more specifically at least about 50%, relative to the Central Elevation in the crotch region exhibited by an essentially identical absorbent article without a shaping line.

As used herein, the terms "crease lines" and "shaping lines" refer to narrow, elongated sections that promote folding by providing a sudden change in material properties of matter along the line relative to matter on either side of the line. Crease lines and shaping lines, as defined herein, can be generally referred to as "bending lines." Such lines can have a width less than about 5 millimeters (mm), desirably less than about 3 mm, more specifically less than about 2 mm, and most specifically between about 0.5 mm and about 1.5 mm. The geometry and nature of bending lines are described more fully hereafter.

As used herein, the "crotch region" of an absorbent article refers to the generally central region that will be in contact with the crotch of the user, near the lowermost part of the torso, and resides between the front and rear portions of the article. Typically the crotch region contains the transverse centerline of the article and generally spans approximately 7 to 10 cm in the longitudinal direction.

As used herein, "elastic modulus" is a measure of slope of stress-strain of a web taken during tensile testing thereof and is expressed in units of kilograms of force. Tappi conditioned samples with a width of 3 inches are placed in tensile tester jaws with a gauge length (span between jaws) of 2 inches. The jaws move apart at a crosshead speed of 10 cm/min and the slope is taken as the least squares fit of the data between stress values of 50 grams of force and 100 grams of force, or the least squares fit of the data between stress values of 100 grams of force and 200 grams of force, whichever is greater. If the sample it too weak to sustain a stress of at least 200 grams of force without failure, an additional ply is repeatedly added until the multi-ply sample can withstand at least 200 grams without failure.

As used herein, the term "extensible" refers to articles that can increase in at least one of their dimensions in the x-y plane by at least 10% and desirably at least 20%. The x-y plane is a plane generally parallel to the faces of the article. The term extensible includes articles that are stretchable and elastically stretchable (defined below). In the case of a sanitary napkin comprising an absorbent core, for example, the article and the absorbent core are desirably extensible both in length and width. The absorbent article, however, may only be extensible in one of these directions, desirably at least in the longitudinal direction. Examples of extensible materials and articles, and their methods of preparation, are disclosed in U.S. Pat. No. 5,611,790, issued Mar. 18, 1997 to Osborn.

As used herein, a bulk material (absorbent matter) is "flexible" if a straight, TAPPI-conditioned (50 percent relative humidity at 23° C.) strip of the material 25 cm long with a cross-section of 1 cm×1 cm can be bent 180° around a 5-cm diameter rod without breaking and without requiring application of more than 6 Newtons of force to the ends of the strip to cause the bending over a 3-second span of time. The same material is "shape retaining," as used herein, if the strip is held in place on the rod for 5 seconds and then remains bent to an angle of at least 300 after the strip is removed from the rod (i.e., the strip is deformed such that the straight portions at the ends of the strip are at an angle relative to each other of at least 30°, with a perfectly straight strip defining an angle of 0°).

As used herein, the term "flexure-resistant" refers to an element which will support a bending moment, in contrast to an element which will support only axial forces. Likewise, as used herein, "flexure resistance" is a means of expressing the flexibility of a material or article and is measured according to the Circular Bend Procedure described in detail in U.S. Pat. No. 5,624,423, issued Apr. 29, 1997 to Anjur et al., herein incorporated by reference in its entirety. Flexure resistance is actually a measurement of peak bending stiffness modeled after the ASTM D4032-82 Circular Bend Procedure. The Circular Bend Procedure of Anjur et al. is a simultaneous multidirectional deformation of a material in which one face of a specimen becomes concave and the other face becomes convex. The Circular Bend Procedure gives a force value related to flexure-resistance, simultaneously averaging stiffness in all directions. For comfort, the absorbent article desirably has a flexure-resistance of less than or equal to about 1,500 grams, more specifically about 1000 grams or less, more specifically still about 700 grams or less and most specifically about 600 grams or less. For shaping performance, the central absorbent section as well as the lower absorbent member can have a flexure resistance of at least about 30 grams, more specifically at least about 50 grams, and most specifically at least about 150 grams.

As used herein, the term "horizontal," refers to directions in the plane of the article that are substantially parallel to the body-side surface of the article, or, equivalently, substantially normal to the vertical direction of the article, and comprises the transverse direction and the longitudinal direction of the article, as well as intermediate directions.

The orientation of components in an article, unless otherwise specified, is determined as the article lies substantially flat on a horizontal surface.

As used herein, "Intrinsic Absorbent Capacity" refers to the amount of water that a saturated sample can hold relative to the dry weight of the sample and is reported as a dimensionless number (mass divided by mass). The test is performed according to Federal Government Specification UU-T-595b. It is made by cutting a 10.16 cm long by 10.16 cm wide (4 inch long by 4 inch wide) test sample, weighing it, and then saturating it with water for three minutes by soaking. The sample is then removed from the water and hung by one corner for 30 seconds to allow excess water to be drained off. The sample is then re-weighed, and the difference between the wet and dry weights is the water pickup of the sample expressed in grams per 10.16 cm long by 10.16 cm wide sample. The Intrinsic Absorbent Capacity value is obtained by dividing the total water pick-up by the dry weight of the sample. If the material lacks adequate integrity when wet to perform the test without sample disintegration, the test method may be modified to provide improved integrity to the sample without substantially modifying its absorbent properties. Specifically, the material may be reinforced with up to 6 lines of hot melt adhesive having a diameter of about 1 mm applied to the outer surface of the article to encircle the material with a water-resistant band. The hot melt should be applied to avoid penetration of the adhesive into the body of the material being tested. The corner on which the sample is hung should be reinforced with hot melt adhesive to increase integrity if the untreated sample cannot be hung for 30 s when wet.

As used herein, the term "polymeric web" refers to a porous or nonporous layer primarily composed of polymeric material, and can be a nonwoven web, a plastic film, a polymeric film, an apertured film, or a layer of foam. Polymeric webs can be used as wicking barriers, baffle layers, backsheets, and, if sufficiently liquid pervious, as topsheets of absorbent articles. A polymeric web can consist of about 50 weight percent or more polymeric material, more specifically about 80 weight percent or more polymeric material, and most specifically about 90 weight percent or more polymeric material. Exemplary materials include polyolefins, polyesters, polyvinyl compounds, and polyamides.

The term "sanitary napkin", as used herein, refers to an article which is worn by females adjacent to the pudendal region that is intended to absorb and contain the various exudates which are discharged from the body (e.g., blood, menses, and urine). While the present invention is shown and described in the form of a sanitary napkin, it should be understood that the present invention is also applicable to other feminine hygiene or catamenial pads such as pantiliners, or other absorbent articles such as incontinence pads. The term "feminine care pad" as used herein is synonymous with sanitary napkin.

The absorbent article comprising an absorbent core can, in addition to being extensible, also be stretchable. The term "stretchable", as used herein, refers to articles that are extensible when stretching forces are applied to the article and offer some resistance to stretching. The terms "elastically stretchable" or "elastically extensible" are intended to be synonymous. These terms, as used herein, mean that when in-plane stretching forces are removed, the article or absorbent fibrous structure will tend to return toward its unextended or unstretched dimensions (or original dimensions). It need not return all the way to its unstretched dimensions, however. It may return to relaxed dimensions between its unstretched dimensions and extended (or stretched dimensions).

As used herein, "thickness" of a fluff pad or other absorbent element refers to thickness measured with a platen-based thickness gauge having a diameter of 7.62 cm at a load of about 0.05 pounds per square inch (psi) [about 35 kilograms per square meter].

As used herein, the term "transverse" refers to a direction which lies within the plane of the absorbent article and is generally perpendicular to the longitudinal direction. The z-direction is generally orthogonal to both the longitudinal and transverse centerlines. The term "lateral" refers to substantially in-plane directions having a predominately transverse component. Likewise, "inwardly lateral compression" refers to compression directed from the longitudinal sides of an article toward the longitudinal centerline thereof.

The degree of elevation of the central absorbent section can be quantified in terms of a Vertical Deformation test. As used herein, "Vertical Deformation" refers to the height increase experienced by the body-side surface of an absorbent article when the longitudinal sides in the crotch reason are gripped and steadily moved inward toward the longitudinal centerline of the article, decreasing the span between the longitudinal sides by 1.5 cm. The Vertical Deformation test apparatus comprises two clamps having a clamp width (longitudinal length of the clamped portion of the edge of the article) of 5 cm. One clamp is stationary and the other is on a track that permits the clamp to slide to increase or decrease the distance between the clamps while keeping the clamp aligned and parallel to the other clamp. The clamps should be tilted downward at an angle of 20 degrees relative to horizontal, such that both outer edges of the absorbent article are slightly elevated relative to the nearest crease line, thus somewhat simulating the positioning of the outward edges of the absorbent article that may be induced by panties with elevated elastic edges in the crotch region. The clamps are 5 cm above the surface of the track, permitting a pad to be suspended in air between the clamps, gripped in the crotch area such that a portion of the longitudinal sides of the absorbent core are held, with the clamps extending inward no more than about 3 mm from the outer edge of the absorbent core. The article should be held substantially taut in the region between the clamps without damaging the article, such that the crotch region is substantially horizontal before lateral compression begins. At a rate of about 0.5 centimeters per second (cm/s), the slidable clamp is moved smoothly toward the fixed clamp by a distance of 50% of the initial width of the article in the crotch region (or less if the article become incompressible such that more than about 5 kg of force is required to further compress the article). The height of the center of the pad or absorbent article is recorded before the clamp is moved and after the clamp is moved, yielding a difference that is reported as the Vertical Deformation. An increase in height is reported as a positive number, while a decrease is reported as a negative number. Desirably, the Vertical Deformation of the absorbent article is at least about 0.5 cm. Specifically, the Vertical Deformation is at least about 1 cm, and more specifically it is at least about 1.5 cm and up to about 10 cm. Desirably, an absorbent article of the present invention exhibits an increase in Vertical Deformation in the crotch region of at least about 20%, and more specifically at least about 50%, relative to the Vertical Deformation in the crotch region exhibited by an essentially identical absorbent article without a shaping line.

As used herein, "Wet Bulk" is based on a caliper measurement of a sample according to the definition of "bulk" above (at 0.344 kPa), except that the conditioned sample is uniformly misted with deionized water until the moistened mass of the sample is approximately 250% of the dry mass of the sample (i.e., the added mass of the moisture is 150% of the dry sample weight). If the sample cannot absorb and retain enough moisture from misting to increase the mass by 150%, then the highest level of achievable moisture add-on below 150% but still above 100% moisture add on should be used. The Wet Bulk in cc/g is calculated as the thickness of the substantially planar moistened sample under a load of 0.344 kPa (0.05 psi) divided by the oven-dry sample basis weight. Absorbent materials in the absorbent members of the present invention can have a Wet Bulk of about 4 cc/g or greater, more specifically about 6 cc/g or greater, more specifically still about 10 cc/g or greater, and most specifically about 15 cc/g or greater, with an exemplary range of from about 5 cc/g to about 20 cc/g.

As used herein, the "wet:dry ratio" is the ratio of the geometric mean wet tensile strength divided by the geometric mean dry tensile strength. Geometric mean tensile strength (GMT) is the square root of the product of the machine direction tensile strength and the cross-machine direction tensile strength of the web. Unless otherwise indicated, the term "tensile strength" means "geometric mean tensile strength." The absorbent webs used in the present invention can have a wet:dry ratio of about 0.1 or greater and more specifically about 0.2 or greater. Tensile strength can be measured using an Instron tensile tester using a 2-inch jaw width, a jaw span of 2 inches, and a crosshead speed of 25.4 centimeters per minute after maintaining the sample under TAPPI conditions for 4 hours before testing. The absorbent webs of the present invention can have a minimum absolute ratio of dry tensile strength to basis weight of about 0.01 gram/gsm, specifically about 0.05 grams/gsm, more specifically about 0.2 grams/gsm, more specifically still about 1 gram/gsm and most specifically from about 2 grams/gsm to about 50 grams/gsm.

DETAILED DESCRIPTION OF THE DRAWINGS

Figure 1:
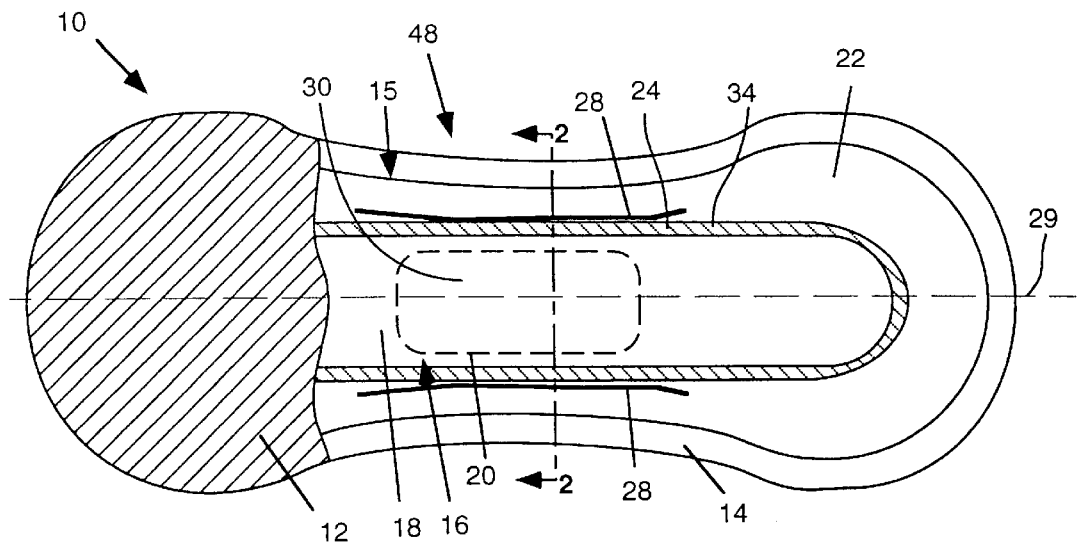
FIG. 1 depicts a top view of a sanitary napkin of the present invention.
Figure 2:
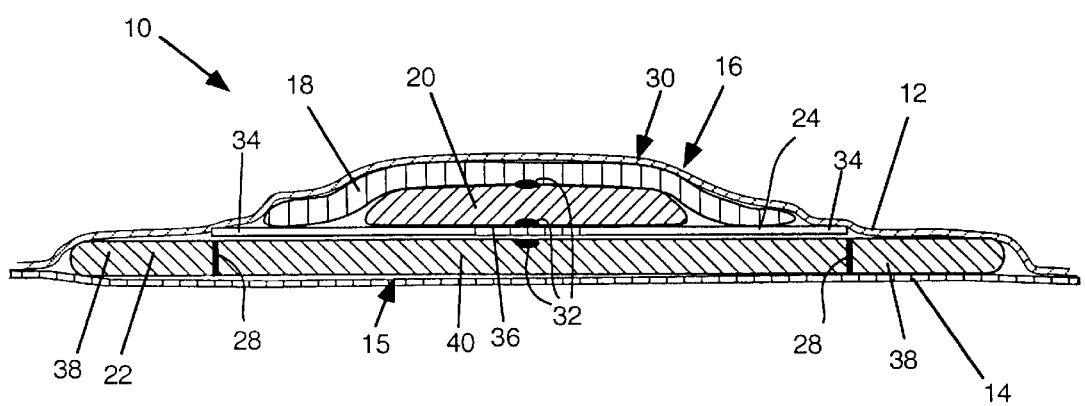
FIG. 2 depicts a cross-section of the sanitary napkin of FIG. 1.

FIG. 1 depicts a top view of an article 10 according to the present invention, with a transverse cross-section therefrom depicted in FIG. 2. The article 10 comprises a liquid pervious topsheet 12, which is cut away in FIG. 1 to reveal underlying components, joined to a backsheet 14 with an absorbent core 15 disposed therebetween. The absorbent core 15 comprises a lower absorbent member 22 and a central absorbent section 16 having an upper absorbent member 18 and a narrower middle absorbent member 20 beneath the upper absorbent member 18. The middle absorbent member 20 desirably lies primarily in the crotch region 48 of the article, where it deforms the upper absorbent member 18 to define a medial hump 30 in the crotch region 48. The middle absorbent member 20 desirably is a pledget of a resilient cellulosic fibrous web. As used herein, a "pledget" refers to an absorbent insert within an absorbent core that is generally used to cause deformation or shaping of an adjoining layer of an absorbent article, and in the present invention, is of use in creating a medial hump 30 for improved fit against the body of the wearer.

Between the central absorbent section 16 and the lower absorbent member 22 lies a horizontal wicking barrier 24 that is wider and desirably also longer than the upper absorbent member 18. The horizontal wicking barrier 24 serves to hinder fluid communication between the central absorbent section 16 and the longitudinal sides of the article 10, particularly the longitudinal sides of the lower absorbent member 22 in the crotch region 48. The horizontal wicking barrier 24 extends a distance beyond the sides of the central absorbent section 16 to form a ledge 34. In one embodiment, the ledge 34 in the crotch region 48 (more generally, the target zone) of the article 10 covers about 25% or more, specifically about 50% or more and most specifically about 80% or more of the surface of the lower absorbent member along the transverse centerline of the article, with essentially 100% coverage in the crotch region 48 being desirable in some embodiments.

The horizontal wicking barrier 24 desirably is substantially planar, though there may be some degree of curvature, bumps, or depressions in the horizontal wicking barrier 24 due to nonplanar structures in the lower absorbent member 22 or due to a void therein.

The horizontal wicking barrier 24 comprises a barrier material that can be a polymeric film or plastic film; a nonwoven web; a layer of rubber, thermoplastic material, silicone, or other non-absorbent materials; or a less pervious paper sheet including, for example, glassine, wax paper, impregnated papers, paper-polymer composites, paper or tissue treated with hydrophobic matter or containing internal sizing to render it less hydrophilic. Desirably, the barrier material will have a porosity less than 20%, more specifically less than 10%, and more specifically the barrier material will be substantially nonporous or substantially impermeable, though apertures 36 can be provided in selected portions of the barrier material to prevent oversaturation of the central absorbent section 16. With apertures 36 added, it is still desirable that the average open area of the barrier material be less than 20% and more specifically less than about 5% in the target zone. The barrier material can have a thickness of about 0.2 mm or less, more specifically about 0.1 mm or less, and most specifically about 0.08 mm or less, with an exemplary range of from about 0.02 mm to about 0.3 mm.

The barrier material desirably has an Intrinsic Absorbent Capacity (hereinafter described) less than about 0.5, more specifically less than about 0.1, and more specifically still approximately 0.

The permeability or porosity or surface chemistry of the horizontal wicking barrier 24 can vary with position along the material such that wicking is delayed or hindered to differing extents at different locations. Specifically, the horizontal wicking barrier may be provided with one or more openings or apertures 36 underneath the middle absorbent member 20 to permit liquid flow to the lower absorbent member 22 from the central absorbent section 16.

The horizontal wicking barrier 24 can comprise a section of the backsheet 14 which extends around or wraps one or more sides of the lower absorbent member 22 (this embodiment is not shown), and then extends a distance on or above the body-side surface of the lower absorbent member 22. Thus, the backsheet material 14 can extend between layers of the absorbent core 15 to define at least a portion of the horizontal wicking barrier 24. The horizontal wicking barrier 24 can also consist substantially entirely of a polymeric web which is unitary with the backsheet 14, meaning that the two components can be formed from a single section of the polymeric web.

The horizontal wicking barrier 24 can comprise a plurality of components, such as two or more sections of polymeric film, or a combination of an impregnated region on the body-side surface of the lower absorbent member and a polymeric film, and the like.

The wicking barrier 24 can have a nonuniform thickness, including features such as bumps or projections from the surface (not shown) that interact with other components in the absorbent article. The wicking barrier 24 may also have ridges or creases to help direct bending of the article or to favorably modify the stiffness and comfort of the article.

The horizontal wicking barrier 24 can have adhesive on both of its surfaces or only one of its top (body side) and lower (garment side) surfaces to help transfer deflection forces across the wicking barrier 24, or, less preferably, it can be substantially free of adhesive.

The width of the middle absorbent member 20 can be less than the width of the upper absorbent member 18 in the crotch region 48 by about 2 mm or greater, more specifically about 5 mm or greater, more specifically still about 8 mm or greater, and most specifically from about 10 mm to about 30 mm. Desirably, the length of the middle absorbent member 20 is approximately equal to the length of the crotch region 48, which generally is less than one half the length of the article 10 and frequently about one third the length of the article 10. Desirably, the middle absorbent member 20 has a thickness greater than that of the upper absorbent member 18, such as a thickness of about 1 mm or greater, and more specifically about 3 mm or greater.

Desirably, the mean pore size of the middle absorbent member 20 is smaller than that of the upper absorbent member 18 such that capillary forces will remove fluid from the upper absorbent member 18 into the middle absorbent member 20 for an improved dry feel.

In one embodiment, the middle absorbent member 20 is a central rising member such as a flattened, rolled tissue or paper structure including "e"-folded materials, with a centerline aligned with the longitudinal centerline 29 of the article 10 (the flat cross-bar of the "e" shape lying in the transverse direction, normal to the longitudinal centerline 29 of the article). Upon lateral compression from the longitudinal sides of the article 10, the flattened "e" shape deflects upwardly, the upper loop of the "e" shape springing back into the approximate shape of a semicircle to urge the upper surface of the central absorbent section 16 toward the body of the wearer.

The upper absorbent member 18 can be preshaped such that its tendency to deflect upward during lateral compression is at least partially independent of the presence of the middle absorbent member 20. For example, the upper absorbent member 18 can be stamped, heat embossed, molded, or otherwise pre-shaped. The upper absorbent member 18 can be a web of fluff pulp reinforced with thermoplastic fibers which is then molded with applied heat or heat-embossed to have an upward-deflecting shape. In one embodiment, the upper absorbent member 18 is an airlaid material or airlaid composite that is formed on a shaped surface, such as a mesh of wires or a porous sintered surface, to impart an intrinsic concave downwards shape. Binder material such as thermoplastic fibers may be present to help create a resilient pre-shaped absorbent material capable of holding its shape even when no middle absorbent member 20 is present and even when the absorbent core 15 is wetted.

Desirably, the upper absorbent member 18 has a rigidity, and specifically at least one of a flexure resistance, elastic modulus, or bending stiffness greater than that of the middle absorbent member 20 and/or the lower absorbent member 22. The increased rigidity of the upper absorbent member 18 helps promote relatively sharp upward folding when compressed laterally. Desirably, the longitudinal sides of the upper absorbent member 18 are attached to the body-side surface of the horizontal wicking barrier 24.

Desirably, the components of the central absorbent section 16 maintain their shape and void volume when wet. For example, the middle absorbent member 20 and/or the upper absorbent member 18 desirably have a degree of wet resiliency, and specifically a Springback Ratio of about 0.7 or greater, as defined in U.S. Pat. No. 5,672,248, issued to Wendt et al. on Sep. 30, 1997, herein incorporated by reference. In another embodiment, the middle absorbent member 20 comprises a pledget of cellulosic fibers reinforced with thermoplastic material such as polyolefin fibers or PET fibers, or stabilized with wet strength agents such as Kymene.

The lower absorbent member 22 desirably comprises cellulosic fibers and generally has two spaced apart crease lines 28 in the crotch region 48 which promote formation of a valley fold along in the lower absorbent member 22 when the article 10 is compressed laterally inward. Desirably, the entire central portion of the absorbent core 15 between the crease lines 28 deflects upward during lateral compression. Toward that end, the lower absorbent member 22 can be attached to the central absorbent section 16 by attachments 30 such as adhesive, thermal, or ultrasonic bonds to prevent downward buckling of the central portion of the lower absorbent member 22. Further, an optional central rising member (not shown) can be disposed beneath or within the absorbent core 15 to further urge upward deflection of the absorbent core 15 during lateral compression.

The lower absorbent member 22 comprises outer absorbent portions 38 and an inner absorbent portion 40 bounded by crease lines 28 which permit the inner absorbent portion 40 to deflect upward, forming an inverted-U shape, for example, when the laterally outward longitudinal sides also deflect upward (sloped like the outer sides of the letter W). A downward fold (valley fold) can then form along the crease lines 28. Preferably, the crease lines 28 are scoremarks formed by sharply creasing the lower absorbent member 22 along a fold made prior to assembling the article. Alternatively, the scoremark can be a notch created by removal of material in the lower absorbent member 22, wherein the notch penetrates at least about 10% of the layer thickness and preferably at least about 20% of the layer thickness. The crease lines 28 can also be formed by embossing.

In general, the absorbent materials of the absorbent core 15, including any of the lower absorbent member 22, the middle absorbent member 20, and the upper absorbent member 18, can comprise one or more plies of wetlaid or airlaid tissue; cellulosic airlaid webs of comminuted fibers (commonly termed "airfelt"); other dry laid webs; cellulose-superabsorbent mixtures or composites; hydroentangled webs comprising cellulosic fibers; composites of synthetic fibers and papermaking fibers; rayon; lyocell or other solvent-spun hydrophilic fibers; cellulosic foams including regenerated cellulose foams; hydrophilic, flexible foams; fiber-foam composites; absorbent nonwoven webs; cotton; wool; keratin fibers; peat moss and other absorbent vegetable matter; the foam-structured fibrous absorbent materials of F.-J. Chen et al. disclosed in the commonly owned, copending U.S. patent application "Fibrous Absorbent Material and Methods of Making the Same," Ser. No. 09/083,873, filed May 22, 1998; or absorbent foams produced from high internal phase emulsions (HIPE) or other means, such as the foams disclosed in U.S. Pat. No. 5,692,939, issued Dec. 2, 1997 to DesMarais. Coform, a hydraulically entangled mixture of pulp fibers and polymer, is also useful for the present invention. Relevant materials are disclosed in U.S. Pat. No. 4,879,170, issued Nov. 7, 1989 to Radwanski et al. and U.S. Pat. No. 5,350,624 to Georger et al. issued Sep. 27, 1994.

The absorbent core 15 may also comprise free flowing absorbent materials such as fiber nits, particularly eucalyptus nits, formed by dispersing high-consistency pulp to entangle fibers into dense bundles. With added debonding agents, surfactants, lubricants, silicone compounds, or the like, substantially free-flowing nits can be formed with a desirable mean particle size less than about 1 mm, suitable for incorporation into an absorbent pocket in the absorbent core of articles of the present invention. Principles for the formation of nits and their incorporation into absorbent articles are disclosed in commonly owned copending application Ser. No.60/129,746, "Absorbent Particles with Nits and Free-Flowing Particles," filed Apr. 16, 1999. Principles for combining nits with superabsorbent particles in absorbent articles are also disclosed in U.S. Pat. No. 5,800,417, issued to K. Goerg-Wood et al., Sep. 18, 1998. The use of other free-flowing particles, such as polymethyl urea spheres, is disclosed in PCT application WO 98/43684 by M. Raidel, Oct. 8, 1998. Discrete pockets of nits or other free-flowing particles in the absorbent core 15 can be formed by adhesively laminated two fibrous webs together with regions of adhesive material joining the webs, according to principles known for formation of pockets of superabsorbent material in U.S. Pat. No. 5,030,314, issued to T. B. Lang, Jul. 9, 1991, or according to other known methods.

Many cellulosic materials can be incorporated in the absorbent materials of the absorbent core 15, including wood fibers, such as bleached kraft softwood or hardwood, high-yield wood fibers, and chemithermomechanical pulp fibers; bagasse; milkweed; wheat straw; kenaf; hemp; pineapple leaf fibers; or peat moss. High-yield fibers can be used to make absorbent members. The fibers can also be crosslinked, sulfonated, mercerized, heat treated, mixed with thermoplastic stabilizer fibers, or treated with wet strength agents. Mixtures of various fibers can be used, including coform, and other mixtures of thermoplastic fibers and wood fibers deposited together in an airlaying process.

The absorbent materials of the absorbent core 15 can comprise chemically modified cellulose, including any known cellulose derivatives, such as 2,3-dialdehyde cellulose or other cellulosic polymers derived therefrom, including those of K. Rahn and T. Heinze in "New Cellulosic Polymers by Subsequent Modification of 2,3-Dialdehyde Cellulose," *Cellulose Chemistry and Technology*, 32: 173–183 (1998), including sodium bisulfite adducts of 2,3-dialdehyde cellulose or various carboxy cellulose compounds. The modified cellulose compounds may be in powder, fiber, or film form. Multilobal fibers or fibers with complex extruded cross-sections can also be incorporated in the present invention.

In another preferred embodiment, at least one component of the absorbent core 15 comprises a molded, three-dimensional high bulk wet laid cellulosic web, such as an uncreped through-air dried web as taught by F.-J. Chen et al. in commonly owned U.S. patent application, Ser. No. 08/912,906, "Wet Resilient Webs and Disposable Articles Made Therewith," filed Aug. 15, 1997; U.S. Pat. No. 5,399,412, issued to S. J. Sudall and S. A. Engel on Mar. 21, 1995; and U.S. Pat. No. 5,672,248, issued to Wendt et al. on Sep. 30, 1997. Such uncreped structures can offer a plurality of flow channels along the surface of the web. When stacked with other planar materials such as a polymer film, void space can still exist adjacent the surface of the tissue web to permit flow of fluid parallel to the plane of the tissue web. Further, the uncreped tissues show excellent wet resiliency and high bulk under load when wet. Without wishing to be limited by theory, it is believed that the three-dimensional surface structures of such textured webs can maintain their shape and bulk when wet because the hydrogen bonds defining the arrangement of the fibers are formed in the molded, three-dimensional state, so the structure does not relax to a flat state when wetted.

The absorbent capacity of the absorbent members can be optimized for the intended use of the article. For some uses, such as in sanitary napkins, it is desirable that the absorbent capacity of the central absorbent section 16 be at least 7 ml of fluid, specifically at least 10 ml, more specifically at least 16 ml, more specifically still at least 20 ml, and most specifically from about 15 ml to about 35 ml. In larger articles such as diapers, the absorbent capacity of the central absorbent section 16 generally should be greater than 60 ml and can be about 300 ml or less of fluid, more specifically about 200 ml or less with exemplary ranges of from about 80 ml to about 250 ml or from about 100 ml to about 300 ml.

In one embodiment, the absorbent capacity of the lower absorbent member 22 is less than the absorbent capacity of the central absorbent section 16, which can be useful, for example, in ultrathin articles. For example, the lower absorbent member 22 can have an absorbent capacity of about 5 to about 100% of the absorbent capacity of the central absorbent section 16, or the ratio can be about 90% or less, more specifically about 70% or less, and more specifically still about 30% or less. In sanitary napkin and related articles, the middle absorbent member 20 can have an absorbent capacity of about 3 ml or greater, more specifically about 5 ml or greater, and more specifically still about 10 ml or greater.

For ultrathin pads and other absorbent articles, it is desirable that the dry components of the absorbent core 15 have a total thickness between about 2 mm and about 15 mm, and more specifically from about 3 mm to about 8 mm. When wetted, the central absorbent section 16 and/or the lower absorbent member 22 may increase substantially in thickness and void volume, such as a thickness increase of about 100% or greater, more specifically about 200% or greater, and more specifically still about 300% or greater. An example of a low-cost cellulosic component capable of increasing in thickness when wet is the absorbent material of Chen and Lindsay disclosed in U.S. Pat. No. 5,865,824, "Self-texturing Absorbent Structures and Absorbent Articles Made Therefrom," issued Feb. 2, 1999 to Fung-Jou Chen and J. D. Lindsay, or the densified structures of Hollenberg et al. in U.S. Pat. No. 5,779,860, "High-density Absorbent Structure," issued Jul. 14, 1998. Regenerated cellulose sponge materials are also capable of expanding significantly when wet and can be used to enhance body fit and conformability by providing the materials in nonuniform basis weights that expand in a three-dimensional shape. Densified cross-linked cellulosic mats can also be used.

Desirably, the topsheet 12 is compliant, soft and nonirritating to the user's skin. It can be made from any of the conventional materials for this type of use. Nonlimiting examples of suitable materials include woven and nonwoven polyester, polypropylene, nylon, rayon or the like, particularly in the form of formed or apertured thermoplastic films, including those described in U.S. Pat. No. 4,324,246 issued to Mullane and Smith on Apr. 13, 1982 and U.S. Pat. No. 4,342,314 issued to Radel and Thompson on Aug. 3, 1982. Mechanically apertured forms can also be used. Other known cover materials can be employed, including those made from textured cellulosic basesheets with hydrophobic matter added to selected portions of the basesheet, particularly the most elevated portions of the basesheet, as described in commonly owned copending U.S. application, "Dual-zoned Absorbent Webs", Ser. No. 08/997,287, filed Dec. 22, 1997. The topsheet 12 desirably is a liquid pervious nonwoven web further provided with apertures in the central regions for effective fluid intake. Also desirably, hydrophilic fibers from the upper absorbent member 18 or other sources extend into the apertures of the topsheet 12 to help promote wicking of body fluids into the apertures and to improve fluid communication between the body and the central absorbent section 16. For example, short hardwood fibers can be added into the apertures of an apertured film or nonwoven web through an airlaid process as the topsheet 12 rests on a thin, gas-permeable layer of absorbent material. Only a few milligrams of added hydrophilic fibers such as bleached eucalyptus in the apertures of a topsheet can improve the wicking performance of an apertured hydrophobic topsheet.

The outer surface of topsheet 12 can be treated with a surfactant to improve liquid penetration, and can have gradients in wettability created by different chemical treatments on the two surfaces of the topsheet 12 or by having different regions in the plane of the topsheet 12 having differing surface chemistry, such that fluid is preferentially absorbed in targeted intake regions and repelled by other regions. Surfactant treatment or application of other wetting agents can be accomplished by any of the common techniques known to those skilled in the art, including, for example, by spraying, by padding or by the use of transfer rolls. Useful wetting agents include polyethylene glycol monolaurates (e.g., PEGOSPERSE 200 ML, a polyethylene glycol 200 monolaurate available from Lonza, Inc., Williamsport, Pa., USA), and ethoxylated oleyl alcohols (e.g., VOLPO-3, available from Croda, Inc., New York, N.Y., U.S.A.). Plasma treatment, electron beams, and corona discharge can also be applied to modify surface chemistry.

The backsheet can be a liquid impervious film and can be impervious to odors, as well. The backsheet, like other components of the article 10, can be stretchable to permit customized fit. The backsheet should be relatively quiet when worn, soft, and non-irritating. The backsheet can comprise any material known in the art of absorbent articles, including polymeric films, low-permeability nonwoven webs, cloth layers desirably comprising an impervious layer or film, or polymer-tissue composites. The backsheet and other components may be biodegradable and/or flushable.

Because an impervious horizontal wicking barrier can be beneath the central absorbent section in many embodiments of the present invention, it is not imperative that the backsheet itself be absolutely impervious, at least not over its entire area, for adequate constraint of fluid in the central absorbent section by an impervious wicking barrier may make the primary function of the backsheet to be providing integrity to the article. Nevertheless, for best results, it is desired that the backsheet be substantially impervious, though it can be breathable to permit transmission of water vapor for comfort. The backsheet can be both breathable and stretchable.

Figure 3:
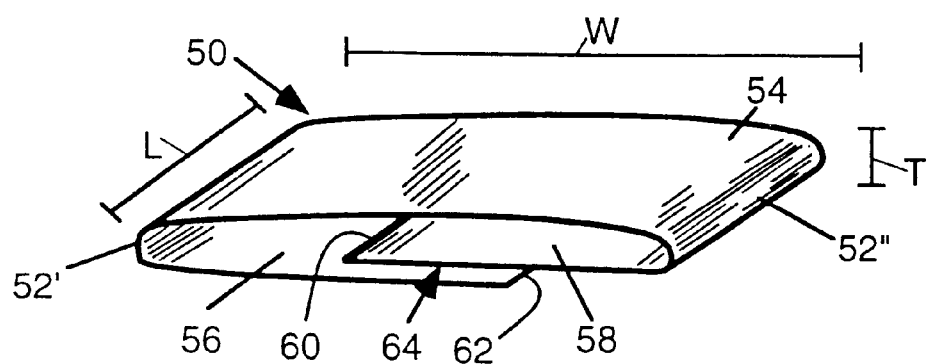
FIG. 3 depicts a central rising member having an "e"-fold construction.

FIG. 3 provides a perspective view of one form of an absorbent central rising member 50 which may serve as a middle absorbent member in an absorbent article (not shown) of the present invention, or may be placed beneath the horizontal wicking barrier (not shown) in articles of the present invention. The central rising member 50 comprises a sheet of material that is folded or wrapped to have two longitudinal sides 52', 52", an upper portion 54, a first lower portion 56 and a second lower portion 58, each of which terminate respectively into ends 60, 62. The terminal portions of the lower portions 56, 58 overlap in an overlapping region 64. The two lower portions 56, 58 in the overlapping region 64 may be free to slide past each other or may be joined in a fixed relationship to prevent sliding of one lower portion relative to the other. In the embodiment shown, the lower portions 56, 58 are freely slidable relative to one another. The central rising member 50 has a transverse width W, a longitudinal length L, and a z-direction thickness T. The width W of the central rising member 50 in the absorbent article prior to use can be equal to or less than the minimum width of the absorbent article in the crotch region. Specifically, the width W of the central rising member 50 can be about 90% or less, more specifically about 70% or less, more specifically still about 50% or less of the minimum width of the absorbent core in the crotch region of the absorbent article. Without limitation, dimensions of width W, thickness, T, and length L for a central rising member 50 suitable for a sanitary napkin and related absorbent articles can include the following, given for the article in its unused, uncompressed state: for width W, from about 10 mm to about 60 mm, more specifically from about 15 mm to about 40 mm; for thickness T, from about 1 mm to about 15 mm, more specifically from about 3 mm to about 8 mm; for length L, from about 10 mm to about 100 mm, more specifically from about 15 mm to about 85 mm, and most specifically from about 30 mm to about 70 mm.

The material forming the central rising member 50 is shown as folded roughly into the shape of a compressed letter "e", with the lower portion 58 corresponding to the central crossbar of an "e" that extends across a portion of the width of the "e". Thus, the folded shape of the central rising member 50 resembles a section of material folded into a tube with overlapping ends 60, 62 in an overlapping region 64, the tube being vertically compressed to be substantially flat. When laterally compressed, the lower portions of the folded material 56, 58 that terminate into overlapping ends 60, 62 can slide toward the opposing longitudinal side of the article. Specifically, the end 60 of the second lower portion 58 slides toward the first longitudinal side 52', while the end 62 of the first lower portion 56 may slide toward the second longitudinal side 52"or can remain immobile or fixed to underlying sections of the article. During such deformation, the upper portion 54 deflects upward.

The central rising member 50 can be a flexible absorbent material such as densified airlaid pulp fibers, coform, or one or more layers of creped or uncreped tissue. It can also comprise nonwoven webs, foam webs, flexible rubber or plastic layers, and the like. In alternate embodiments, a central rising member can be a resilient web folded as a flattened tube or an equivalent, such as the shape of the letter "C" rotated clockwise by 90 degrees.

Preferably, the central rising member 50 should be resilient enough that it can lift a load of 50 grams by at least 4 mm when it is resting on a solid surface and the longitudinal sides are laterally compressed toward the longitudinal centerline of the central rising member 50 such that the longitudinal sides thereof are brought no more than 13 mm closer due to lateral compression. Rectangular blocks 50 mm long and 5-mm square in cross section, with the 2-inch long dimension aligned with the longitudinal sides of the central rising member, can be used to evenly displace the longitudinal sides toward one another. The load to be lifted is a vertically oriented spindle on a device such as a Mitutoya Digimatic Indicator (e.g., Model 543-525-1, with the spindle appropriately modified for the correct load). A section of acrylic plastic 0.7 mm in thickness, 50 mm long and 20 mm wide is placed over the central rising member 50 and centered beneath the spindle of the indicator to evenly distribute the load of the spindle. The vertical displacement caused by the lateral compression of the longitudinal sides of the central rising member 50 is the vertical distance traveled by the spindle.

Figure 4A:
FIG. 4 depicts a central rising member in various stages of lateral compression.
Figure 4B:
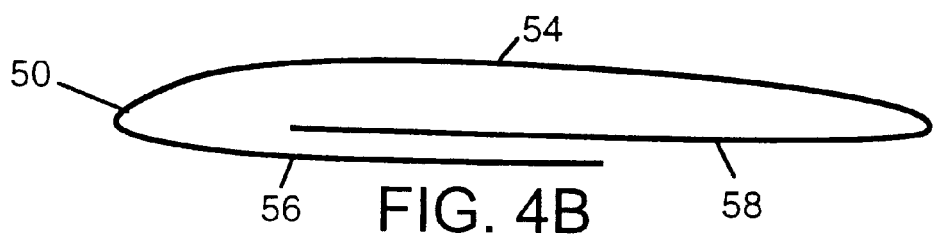
Figure 4C:
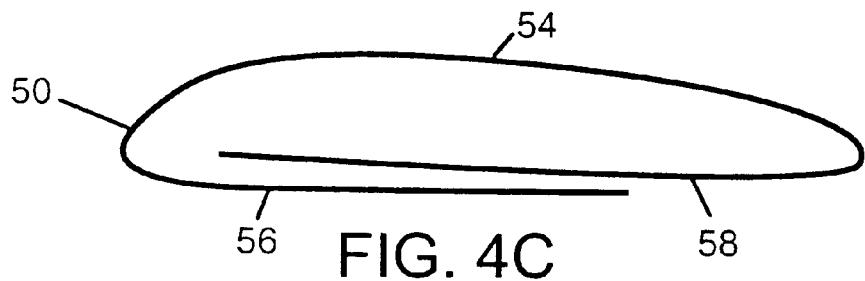
Figure 4D:
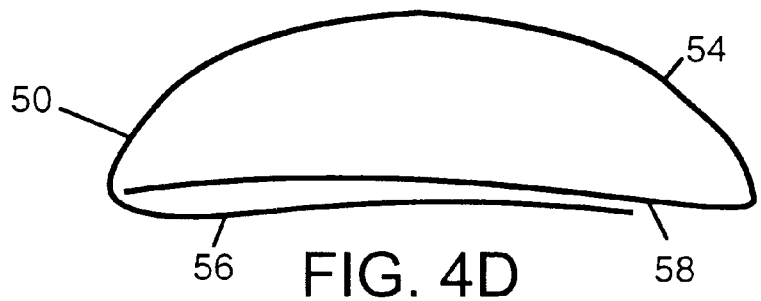

FIG. 4 depicts the central rising member 50 in several states of deformation, beginning in FIG. 4A with a vertically compressed central rising member 50 under little or no lateral compression, with successively greater degrees of lateral compression and vertical buckling being displayed in FIGS. 4B through 4D.

Figure 5:
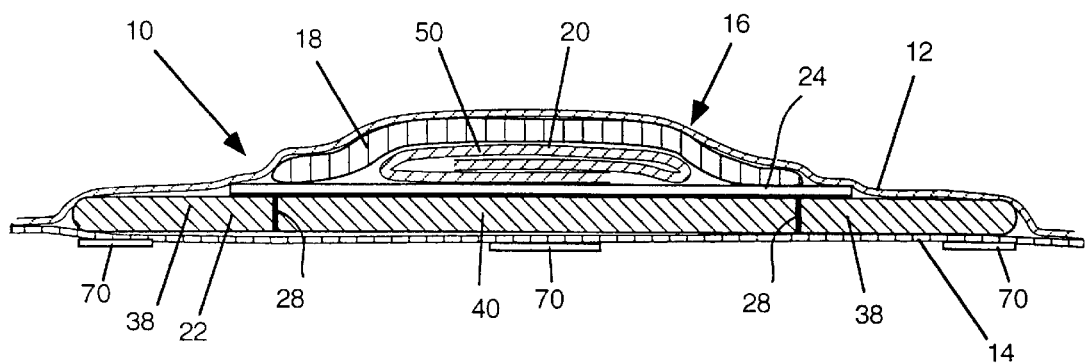
FIG. 5 depicts a sanitary napkin having a central rising member in the central absorbent section.

FIG. 5 depicts a cross section along the transverse centerline of one embodiment of an absorbent article 10 according to the present invention. Here the middle absorbent member 20 is also a central rising member 50, depicted as an e-folded absorbent web. Here the crease lines 28 are approximately directly underneath the longitudinal sides of the upper absorbent member 18.

The garment side of the backsheet 14 is further provided with pressure-sensitive adhesive strips 70 and release paper (not shown) for effective attachment to the garments of the wearer. The adhesive strips may further comprise microcapsules containing agents that are not released until the release liner is removed, which breaks some of the microcapsules, as taught in U.S. Pat. No. 5,591,146, issued Jan. 7, 1997 to Hasse. The microcapsules can contain odor control agents, perfumes, skin wellness agents, and the like.

Figure 6:
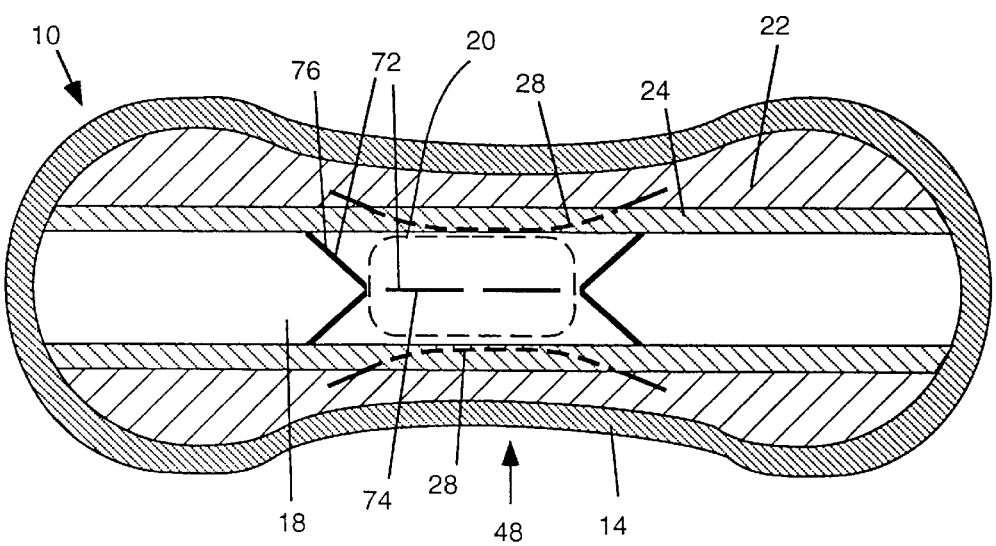
FIG. 6 depicts a top view of an absorbent article with bending lines in the upper absorbent member.

FIG. 6 depicts the top view of a sanitary napkin 10 according to the present invention having arcuate crease lines 28 in the lower absorbent member 22 extending beneath the horizontal wicking barrier 24. The topsheet is not shown for clarity.

The upper absorbent member 18 comprises an optional shaping line 72 comprising two sets of outward spanning lines 76 at the longitudinal ends of a central longitudinal line 74, which, as drawn comprises two short sections. The outward spanning lines 76 preferably comprise slits, perforations, or other stiffness reducing means. When compressed laterally in the crotch region, the article 10 should deform to form valleys along the crease lines 28 in the crotch region 48 and form an elevated central region in the upper absorbent member 18, with deflection governed in part by the presence of the middle absorbent member 20.

Figure 7A:
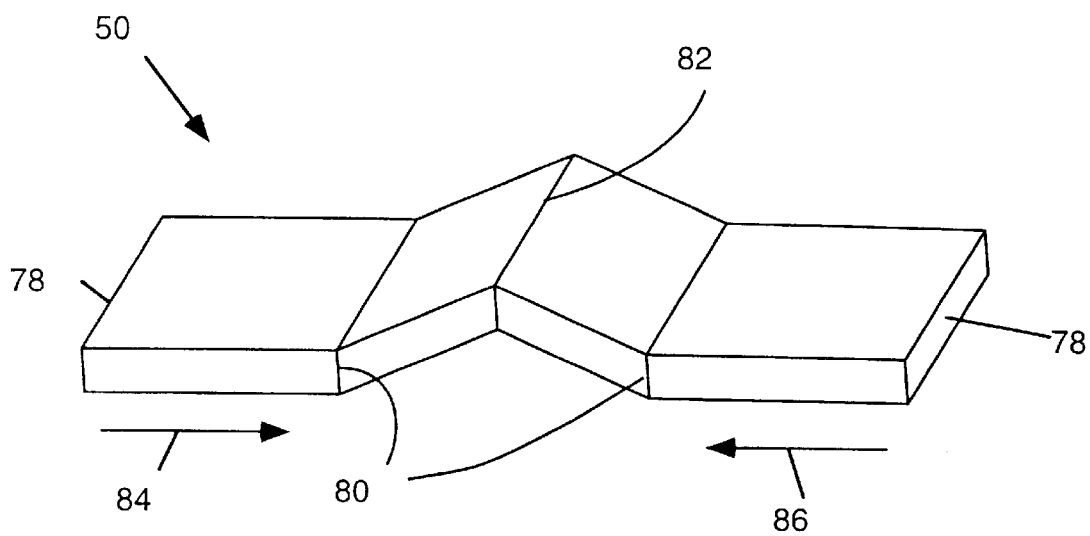
FIGS. 7A and 7B depict two forms of the central rising member.
Figure 7B:
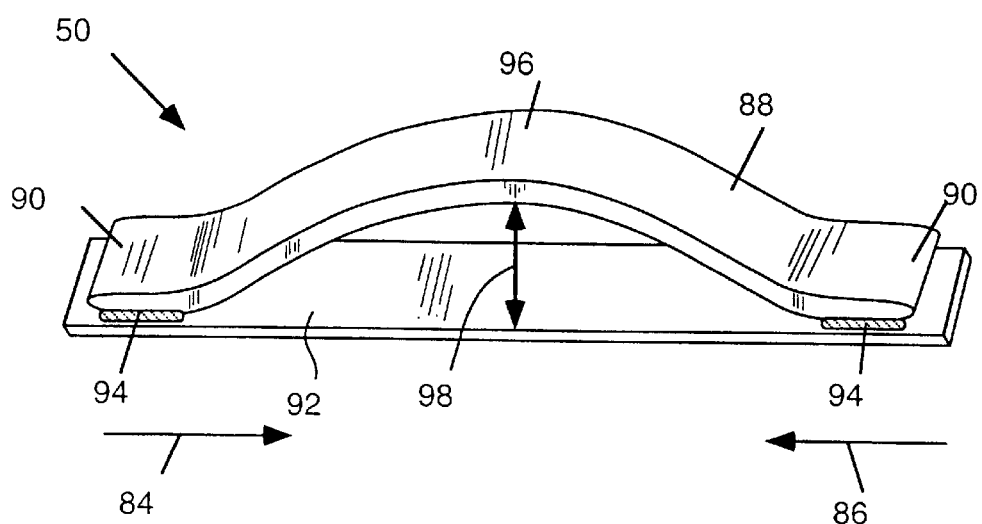

FIGS. 7A and 7B depicts two types of central rising members 50. FIG. 7A depicts a central rising member 50 having longitudinal sides 78, two crease lines 80, and a longitudinal central hinge 82 or shaping line for upward folding. Central rising member 50 forms an inverted V-shape when the longitudinal sides 78 are moved inward toward the initial longitudinal centerline of the central rising member 50 (i.e., in the directions indicated by arrows 84, 86), increasing the apparent thickness of the central rising member 50 and vertically deflecting the upper absorbent member (not shown).

The central rising member 50 can placed above a horizontal wicking barrier and attached thereto by adhesive deposits near the longitudinal ends 78 of the central rising member 50. Other bonding or joining means can be used.

FIG. 7B depicts a central rising member 50 related to that of FIG. 7A, but one that is substantially free of creases or hinge elements. The central rising member 50 comprises a resilient web 88 having ends 90 that are anchored to an underlying web 92 by bond areas 94 which can be adhesive bonds or thermal welds and the like. The length of the resilient web 88 between the bonds areas 94 is greater than the linear distance between the bond areas 94, such that the resilient web 88 forms a loop that is convex toward the body side of the wearer. Prior to compression and in an unloaded state, the central rising member 50 has a gap between the central portion 96 of the resilient web 88 and the underlying web 92 defining a distance 98 which can be about 0.5 mm or greater, and preferably less than about 3 mm, such as a gap height of about 0.7 mm to about 2 mm. When subjected to laterally inward compression, wherein the ends 90 of the resilient web 88 are moved toward one another in the respective directions shown by arrows 84, 86, the gap height 98 increases and the central portion 96 of the resilient web 88 moves vertically upward toward the body of the wearer. (As drawn, the gap height is exaggerated or clarity.)

In one embodiment, the resilient web 88 in FIG. 7B comprises multiple layers of thin, flexible material such as tissue or layers of polymeric film which have been previously bent or preshaped to be predisposed to flex upward during laterally inward compression, and specifically, geometrically predisposed to flex upward.

Figure 8A:
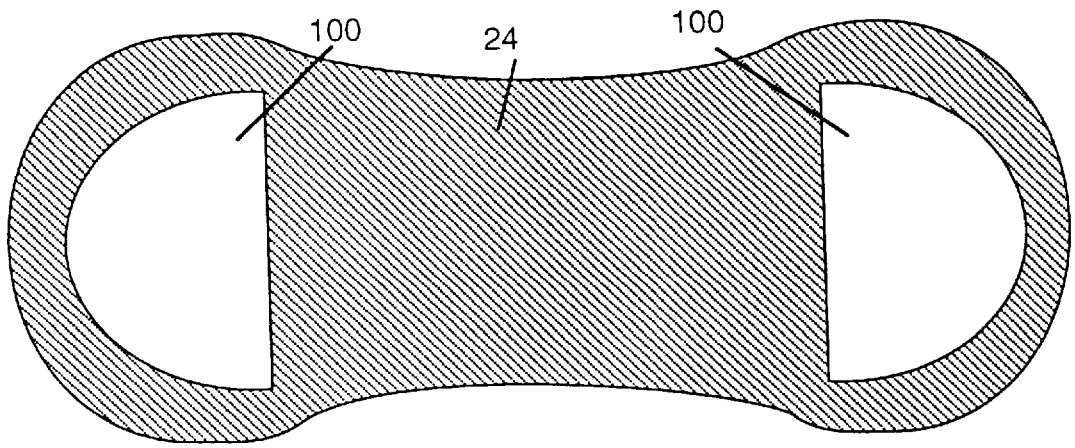
FIGS. 8A–8C depict various arrangements of holes in a horizontal wicking barrier.
Figure 8B:
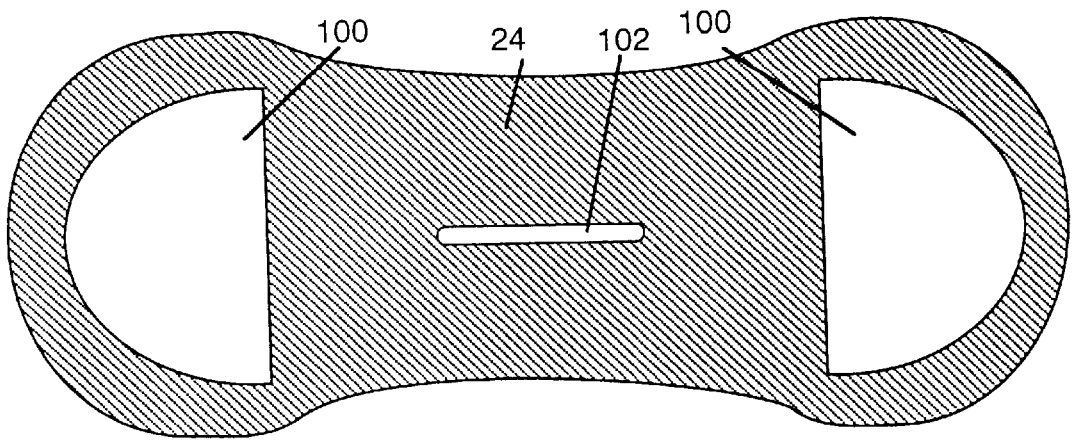
Figure 8C:
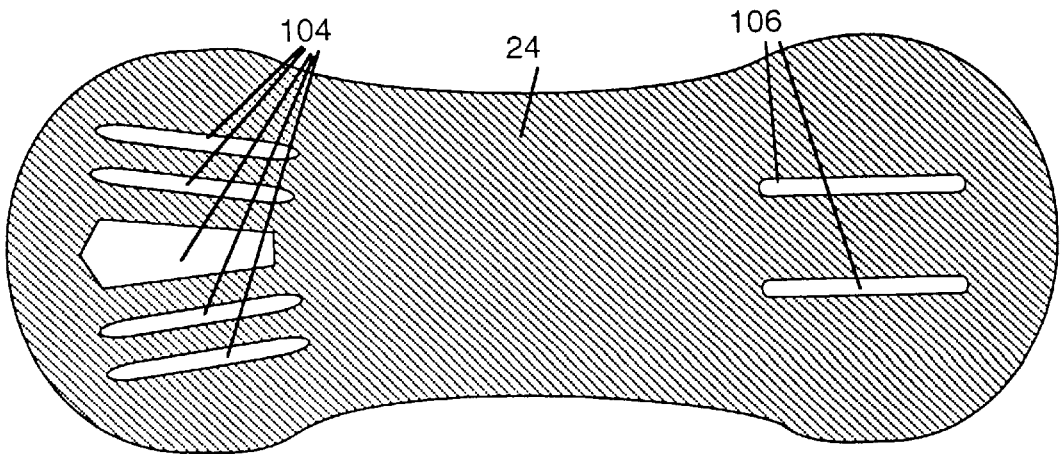

FIGS. 8A–8C depict three forms of a horizontal wicking barrier 24 for a dogbone-shaped absorbent article (not shown), with the different horizontal wicking barriers being distinguished by the nature of holes therein to permit passage of fluid from a central absorbent section (not shown) to an underlying lower absorbent member (not shown). In these embodiments, the periphery of the horizontal wicking barrier is intended to extend to or beyond the periphery of the lower absorbent member and may correspond to the size and shape of the backsheet (not shown). In FIG. 8A, semicircular or semi-elliptical holes 100 are provided in the longitudinal end portions of the horizontal wicking barrier 24 to permit fluid to migrate from the central absorbent section to the lower absorbent member only when the central absorbent section has become wetted in the longitudinal ends thereof. FIG. 8B is similar to FIG. 8A, comprising an additional central slot 102 to permit a small degree of wicking or flow of fluid from the central portion of the central absorbent section to the lower absorbent member. FIG. 8C shows another embodiment with holes 104 at one longitudinal end being substantially different in open area and shape than holes 106 in the other longitudinal end of the horizontal wicking barrier 24. In this case, the horizontal wicking barrier 24 is intended for an absorbent article having distinct front and back portions, wherein one portion is intended to receive more flow than the other. Small substantially circular or polygonal apertures, such as holes less than 1 mm in diameter, can further be provided in the horizontal wicking barrier, especially in the central portions intended to reside under a central absorbent section.

Figure 9A:
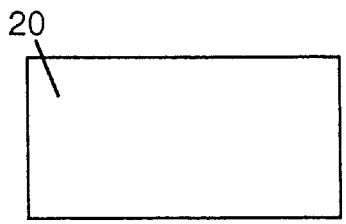
FIG. 9 depicts various shapes of the middle absorbent member.
Figure 9B:
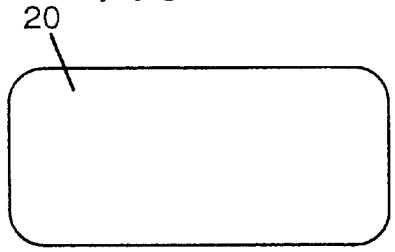
Figure 9C:
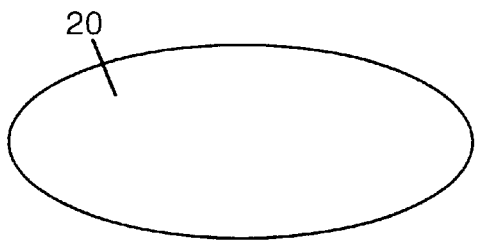
Figure 9D:
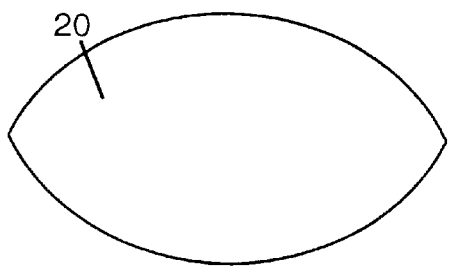
Figure 9E:
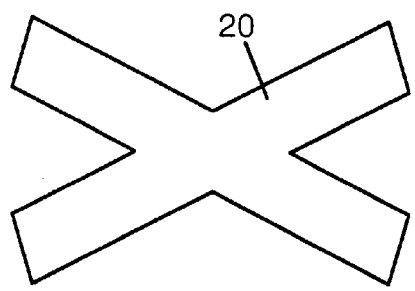
Figure 9F:
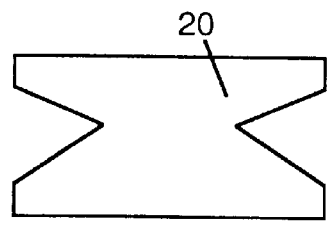
Figure 9G:
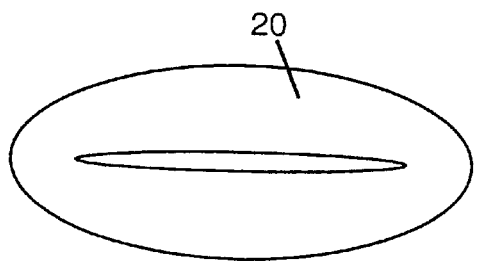

FIGS. 9A–9G depict a variety of different shapes for a middle absorbent member 20, including a parallelogram (FIG. 9A), a rounded parallelogram (FIG. 9B), an ellipse (FIG. 9C), a lemon shape (FIG. 9D), an X-shape (FIG. 9E), an anvil shape (FIG. 9F), and an annular ellipse (FIG. 9G). The shape of the middle absorbent member 20 can affect the deformation of the lower absorbent member and the upper absorbent member in the article, as well as stiffness and comfort in the crotch region. One embodiment uses shapes that are substantially narrower in at the longitudinal ends that at the transverse centerline of the article, such as those in FIGS. 9C, 9D, and 9G. Alternatively, the shapes can be substantially rectangular, or have ends wider than the center. Without wishing to be bound by theory, it is believed that substantially rectangular shapes, such as in FIGS. 9A and 9B, provide for more comfortable folds in the absorbent article and for better folding, while better promoting an elevated central portion along the longitudinal centerline of the article and while offering ease of manufacture. However, other shapes can also be used to advantage for particular purposes.

Figure 10:
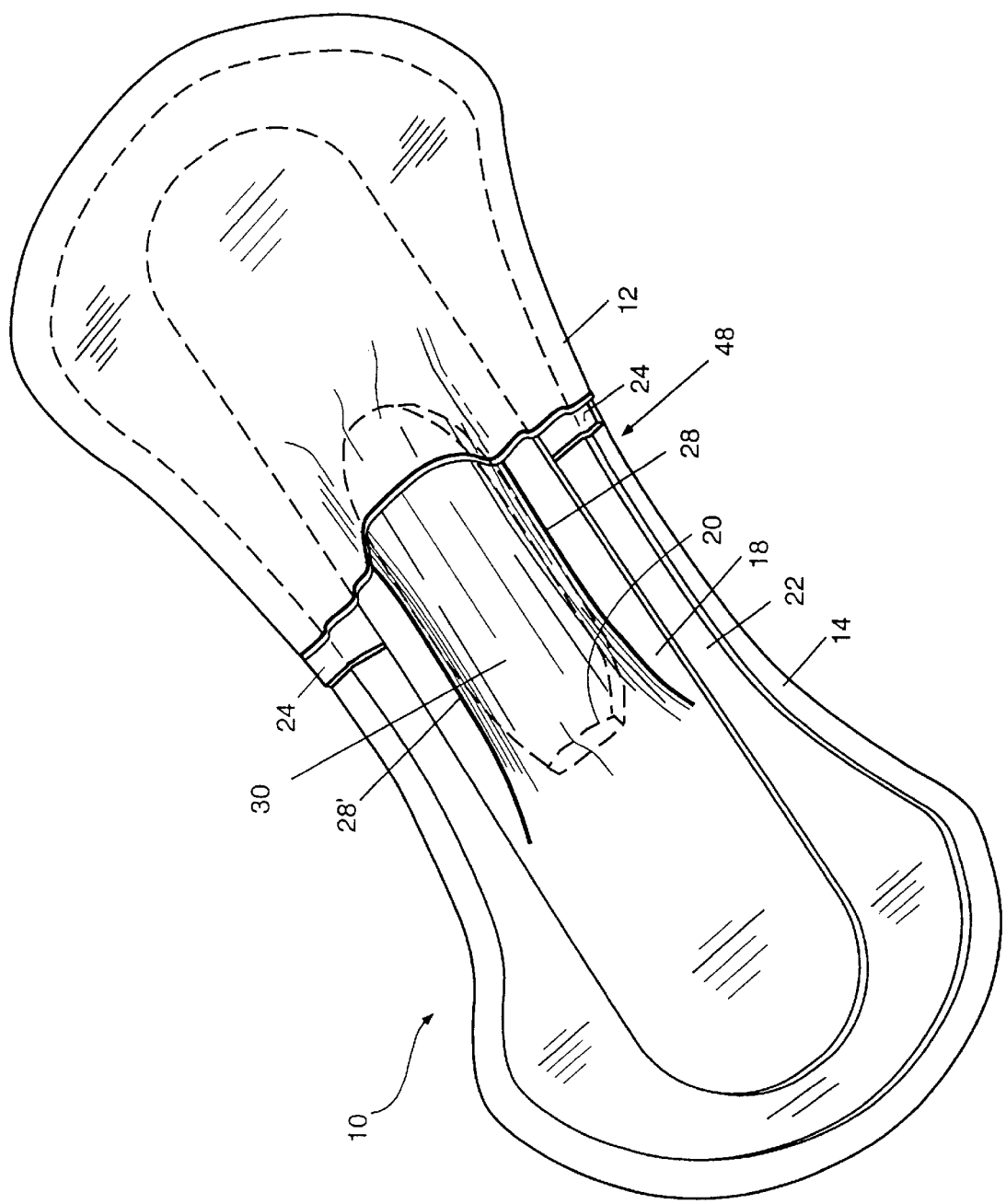
FIG. 10 is a cut away view of a sanitary napkin having a medial hump formed by a thick middle absorbent member superposed on a horizontal wicking barrier.

FIG. 10 is a partial cutaway view of an absorbent article 10 according to the present invention. The topsheet 12 is cut away to reveal several underlying components, particularly the upper absorbent member 18, which has a medial hump 30 therein due to the presence of the underlying middle absorbent member 20, depicted here in a truncated oval shape having a thickness substantially greater than the thickness of the upper absorbent member 18. The upper absorbent member 18 further comprises a pair of substantially longitudinal crease lines 28 in the crotch region 48, the crease lines 28 being spaced apart about the longitudinal centerline of the article 10. The crease lines 28 are transversely outside the longitudinal sides of the middle absorbent member 20 and within the longitudinal sides of the upper absorbent member 18. The crease lines 28 also extend into the underlying lower absorbent member 22, which also has a thickness substantially less than the middle absorbent member 20 (although the middle absorbent member 20 optionally could be thinner than either or both of the upper absorbent member 18 and the lower absorbent member 22). Thus, the crease lines 28 in both the upper absorbent member 18 and the lower absorbent member 22 permit upward folding of the outer longitudinal sides of the lower absorbent member 22 and the upper absorbent member 18 to form a valley fold when the absorbent article 10 is laterally compressed inward by the legs of the user when worn, while the elevated middle absorbent member 20 helps contribute to the formation of a central hump 30 when compressed laterally inward to give an overall W-shape to the article (with the central part of the W-shape desirably being substantially rounded).

The upper absorbent member 18 and the middle absorbent member 20 are separated from the lower absorbent member 22 by the horizontal wicking barrier 24, which extends past the periphery of the lower absorbent member 22 and joins the backsheet 14 at the periphery.

Figure 11:
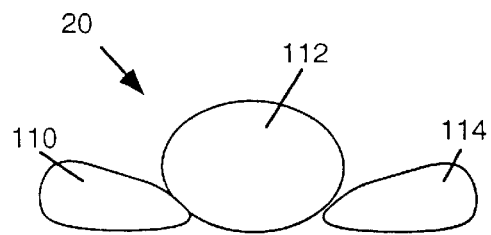
FIG. 11 depicts a traverse cross-section of a middle absorbent member having absorbent material divided into three longitudinally extending pockets.

FIG. 11 depicts a transverse cross section of a middle absorbent member 20 having absorbent material divided into three longitudinally extending pockets 110, 112, 114. Two outer pockets of absorbent material 110, 114 are separated by a central pocket 112 of absorbent material having greater height than the outer pockets 110, 114. The pockets can be individually encased in tissue, a nonwoven web, or may not be encased. Alternatively, folds of material from the topsheet (not shown) or the backsheet (not shown) may partially separate the pockets of absorbent material 110, 112, 114. The central pocket 112 may also comprise loose fibrous nits or absorbent free-flowing particles. When the middle absorbent member 20 is compressed laterally inwardly, the outer pockets 110, 114 will act as wedges to further elevate the central pocket 112 toward the body of the wearer.

Figure 12:
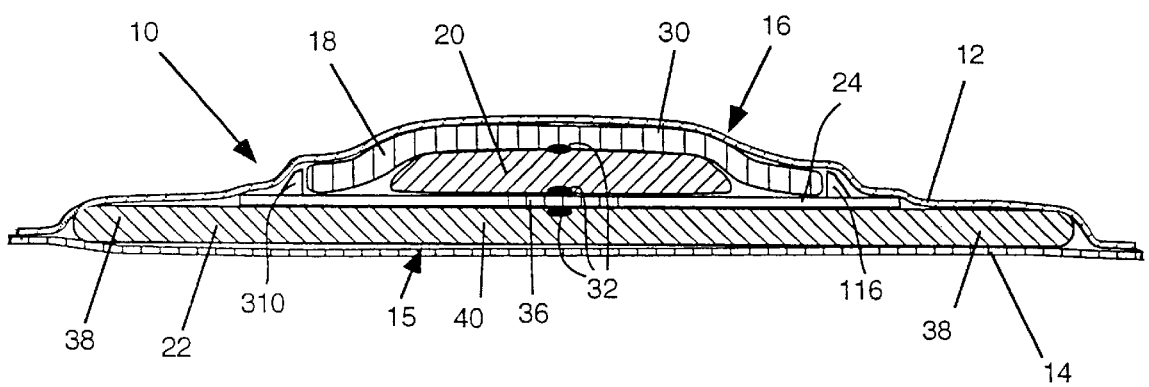
FIG. 12 depicts a transverse cross-section of an absorbent article wherein the horizontal wicking barrier comprises longitudinal upward projections near the longitudinal sides of the horizontal wicking barrier.

FIG. 12 depicts a transverse cross section of an absorbent article 10 similar to that of FIG. 2, except that upward longitudinal projections 116 extending from the horizontal wicking barrier 24 restrain the longitudinal sides of the upper absorbent member 18 in the central absorbent section 16 as it rests on the middle absorbent member 20. The longitudinal projections 116 are longitudinally flexible (i.e., they can flex in the longitudinal direction) yet have sufficient stiffness to promote a valley fold in the absorbent core 15 when the article 10 is laterally compressed, or have sufficient rigidity to restrain the longitudinal sides of the upper absorbent member during lateral compression. The upward longitudinal projections 116 on the horizontal wicking barrier 24 can influence folding of the article 10 during lateral compression in a manner analogous to the crease lines 28 in article 10 of FIG. 2. Crease lines are now optional (and not shown) in the article 10 of FIG. 12, although crease lines desirably can be provided in the lower absorbent member 22, preferably substantially vertically aligned with the upward projections 116 in the horizontal wicking barrier 24. The longitudinal upward projections 116 can be fused to the horizontal wicking barrier 24, and can be thermoplastic elements having a width of from about 0.3 to 3 mm and a height of from about 0.2 mm to about 5 mm, specifically from about 0.5 mm to about 2 mm. The longitudinal upward projections 116 also can be integrally formed with the horizontal wicking barrier 24 by extrusion, molding, cast coating of a thermoplastic, etc., or the longitudinal upward projections on the horizontal wicking barrier can be separately formed regions that are added to a film or other barrier material by gluing, thermal bonding, ultrasonic bonding, or the like. The longitudinal upward projections 116 can extend longitudinally in the crotch region for a length of from about 10 mm to 100 mm, and can be a series of discrete projections or bumps substantially aligned in lines. The stiffness and thickness of the horizontal wicking barrier 24 and the longitudinal upward projections 116 should be optimized to provide good shaping control of the pad without unduly interfering with fluid flow or comfort of the article 10. It is expected that the use of longitudinal upward projections 116 will generally require a relatively stiffer or thicker horizontal wicking barrier 24, such as one with a thickness from about 0.2 mm to about 1 mm.

Figure 13A:
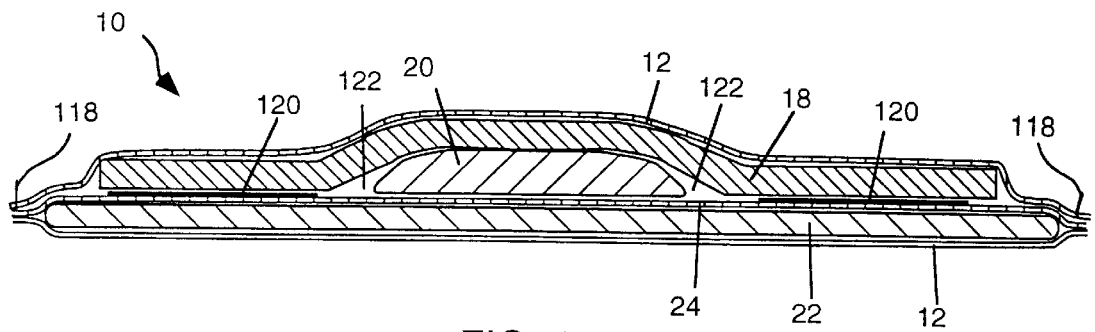
FIGS. 13A–13C depict longitudinal cross-sections of three embodiments of an absorbent article with differing middle absorbent members.
Figure 13B:
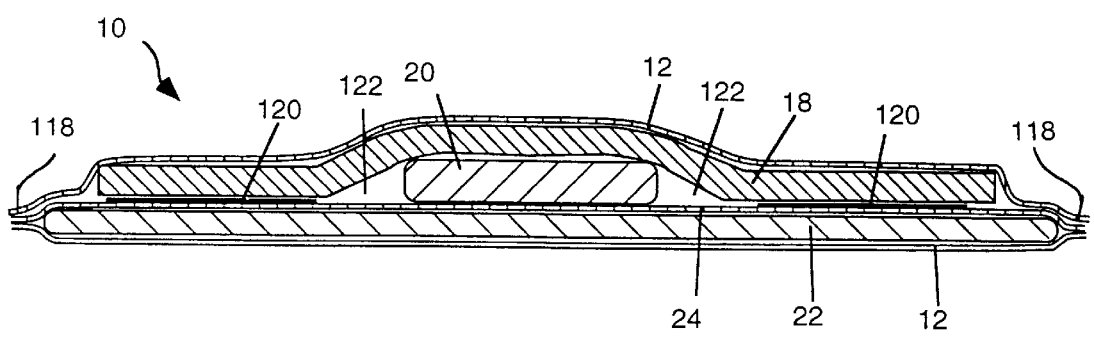
Figure 13C:
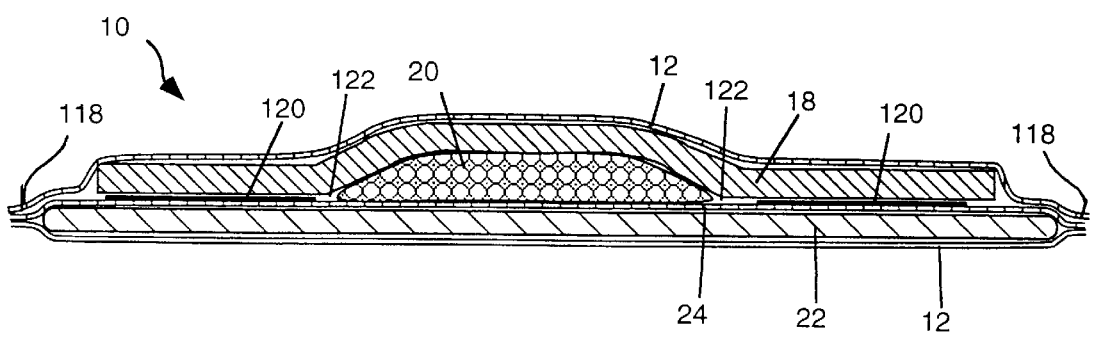

FIGS. 13A–13C depict the longitudinal cross-section of an absorbent article 10 according to the present invention taken along a longitudinal centerline (see, for example, the longitudinal centerline 29 of FIG. 1), showing three alternatives for the middle absorbent member 20. The cross-sectional views in FIGS. 13A–13C are orthogonal to the transverse cross-sectional views described earlier and are intended to depict how various components may be inter-related and connected over the longitudinal length of the article 10. In FIG. 13A, the article 10, the middle absorbent member 20 is tapered and shorter than the upper absorbent member 18. Adhesive zones 120 join a portion of the upper absorbent member 18 to the horizontal wicking barrier 24. The topsheet 14 joins the backsheet 12 and optionally the horizontal wicking barrier 24 at the longitudinal ends 118 of the article 10. A void space 122 exists between the upper absorbent member 18 and the horizontal wicking barrier 24 near the longitudinal ends of the middle absorbent member 20. It is preferred that no adhesive be present to join the upper absorbent member 18 to the horizontal wicking barrier 24 in the region adjacent the longitudinal ends of the middle absorbent member 20 to promote formation of the void space 122 and to allow expansion of the void space 122 when the article 10 is bunched or laterally compressed. In other words, when the article is worn and experiences lateral compression, the deformation of the upper absorbent member 18 can not only enhance contact with the body, but can lead to an expanded void space 122 which can permit fluid to descend through the upper absorbent member 18 even when the upper absorbent member 18 is saturated, to be received by the void space 122, from which the fluid may further move into the middle absorbent member 20 or the lower absorbent member 22.

FIGS. 13B and 13C are identical to FIG. 13A except that the tapered middle absorbent member 20 of FIG. 13A has been replaced with other configurations. FIG. 13B depicts a middle absorbent member 20 that is not substantially tapered longitudinally, which forms a larger void space 122 than in FIG. 13A. FIG. 13C depicts a particulate middle absorbent member 20 comprising a layer of free-flowing absorbent particles such as nits, hollow microspheres, or macrobeads. The void space 122 is considerably reduced in size by virtue of the conformability of the particulate middle absorbent member 20 to the space between the upper absorbent member 18 and the horizontal wicking barrier 24. However, the void space 122 can still expand when the article is worn and provide a space for receiving and directing flow of fluid. The particulates in the particulate middle absorbent member 20 can be restrained by a liquid pervious encasement, such as a nonwoven or tissue web (not shown), or by the lower absorbent member 22 and upper absorbent member 18.

Without limitation, further principles for construction of absorbent articles according to the present invention are given below in terms of the specific components.

OTHER CONFIGURATIONS AND ADDITIONAL COMPONENTS

The absorbent articles of the present invention can comprise a topsheet or a backsheet or both a topsheet and a backsheet, or other means to provide integrity to the article and comfort on the body side surface. An article can be made without a topsheet and/or without a backsheet, particularly if other components are present to provide suitable integrity of the product and liquid barrier functions. For example, a horizontal wicking barrier can be attached to the central absorbent section by attachment means including adhesives, ultrasonic bonds, threads, fiber-fiber entanglement, hook and loop structures, embossments, thermal bonds, elastic ligaments, and other means known in the art to hold the central absorbent section in place. The wicking barrier may also be attached to the lower absorbent member by similar attachment means to hold it in place. Thus, the restraining or integrity-providing effect of the topsheet and backsheet in normal absorbent articles could be replaced by a horizontal wicking barrier suitably attached to the other components of the article. The wicking barrier may also wrap the lower absorbent member to hold it in place and provide a liquid barrier function around or beneath that member. Comfort, softness, and dry feel functions of a conventional topsheet can be replaced by using suitable absorbent materials, particularly those that have been provided with additional hydrophobic material on the surface of the absorbent material to permit fluid intake yet provide a dry feel against the skin.

The absorbent articles of the present invention can be combined with other functional materials internally (as by adding material into the absorbent material or on the barrier material) or externally (as by joining with additional layers), including but not limited to odor absorbing components such as baking soda, talc powder, cyclodextrin, chelating agents such as ethylenediamine tetra-acetic acid, perfumes, zeolites, activated silica, and activated carbon granules, fabrics or fibers; superabsorbent particles and fibers; fluoropolymers; antimicrobial agents including the silver-loaded zeolites of BF Technologies, located in Beverly, Massachusetts, sold under the trademark HEALTHSHIELD™, as well as triclosan products, chitosan or chitin derivatives; enzymes; ion exchange materials or enzyme inhibitors such as urease inhibitors to prevent the production of ammonia, as disclosed in European Patent Application 564,307-A1, "Antiskin Rash Preparation," S. Levi, published Oct. 6, 1993, lipase-inhibiting agents, including those disclosed in European Patent 117,613 B2, "Disposable Absorbent Article Incorporating Agents for the Treatment and Prophylaxis of Diaper Rash and Diaper Dermatitis," issued to K. W. Buckingham, Mar. 24, 1993, and in U.S. Pat. No. 4,556,560, issued to K. W. Buckingham Dec. 3, 1985. Petrolatum, emollients such as lanolin, or skin wellness agents such as aloe vera extract or vitamin E also be incorporated in the absorbent article or on the body-side surface of the absorbent core, the topsheet, or exposed portions of the horizontal wicking barrier.

The absorbent core of the present invention can comprise superabsorbent particles, such as from 5% to 90% by mass superabsorbent particles on a dry mass basis, or from about 30 to about 70% superabsorbent particles, alternatively from about 10% to about 50% superabsorbent particles and more specifically from about 10% to about 40% superabsorbent particles. Superabsorbent material can be incorporated as loose particulates, particles bound to the hydrophilic fibers, superabsorbent fibers, or as a component of the binder material or structuring composition. Superabsorbent material can also be provided in the form of a foam.

In one embodiment, the absorbent core comprises a laminated or layered structure having superabsorbent particles or fibers present in at least one layer. The superabsorbent material can also serve as a binder to hold the fibrous composite in a densified state. Superabsorbent particles can also be retained in discrete, spaced apart pockets, with intervening regions substantially free of superabsorbent particles or having a lesser concentration of superabsorbent particles. Methods for creating pockets of particulate material between two layers of fibrous material are disclosed in U.S. Pat. No. 5,030,314, issued to T. B. Lang, Jul. 9, 1991.

Superabsorbent material bonded to cellulosic fibers can also be beneficial for use in the present invention. For example, binders may be used to join the superabsorbent particles to cellulosic fibers, as disclosed by Hansen et al. in U.S. Pat. No. 5,547,745, issued Aug. 20, 1996, and U.S. Pat. No. 5,693,411, issued Dec. 2, 1997. Further, superabsorbent particles may be adhesively attached to other absorbent materials by entraining the superabsorbent particles in air and passing the particles through a stream of adhesive, wherein the surfaces of the particles become partially coated or treated with adhesive. The adhesive stream may be filaments of a hotmelt extruded from a fine die or spinner and entrained in air, or it may be a spray of a liquid such as a hotmelt, solution, or suspension.

The absorbent core and particularly the absorbent material of the central absorbent section can comprise cellulosic fibers stabilized with a binder material. Likewise, the multiple layers that can be used in the lower absorbent member or the central absorbent section can be joined together with a binder material, or a binder material can attach the topsheet and/or the backsheet to the adjoining lower absorbent member or central absorbent section to improve pad integrity. The binder material may be water swellable or not water swellable. For best results in absorbent articles, the binder material desirably is substantially water insoluble, even when the binder material is water swellable. Preferably, the binder material provides not only good dry stability but also good wet stability and wet resiliency to the absorbent fibrous structure when wetted with liquid water. For applications where wet resiliency is needed to maintain high void volume even under compressive loads, the binder material desirably is not water swellable, is desirably water insoluble, and desirably has a binder wet strength to dry strength ratio of about 10% or greater, specifically about 20% or greater, more specifically about 40% or greater, and most specifically about 50% or greater. The same desirable ranges for binder wet strength to dry strength ratio apply to swellable binder materials as well.

For feminine care articles, tabs and wings can be added to the sides of the absorbent article. The wicking barrier can extend to the beginning of the tab or wing or beyond, though desirably the wicking barrier prevents lateral wicking of fluid into the region of the tab or wing. In one embodiment, the wicking barrier comprises a transverse section which extends laterally past the absorbent core to form a component of wings or tabs. Such a section can be an integral part of the wicking barrier or can be a second wicking barrier member in addition to a first wicking barrier member contained within the absorbent core.

For diapers and disposable training pants, a variety of additional components for body fit and comfort can be added. For example, diapers of the present invention preferably can further comprise side panels, elasticized leg cuffs, elasticized waistbands, and a fastening system preferably comprising a pair of securement members and a landing member. For bowel movement containment, the article may also be provided with flaps, void spaces in the absorbent core, raised barriers or dams, or any other systems for bowel movement containment known in the art.

The entire absorbent article may comprise extensible materials, including corrugated or foreshortened absorbent materials capable of stretch in one or more in-plane directions and an extensible topsheet and backsheet, and optionally an extensible or elastomeric wicking barrier. Several useful configurations for extensible articles are disclosed in U.S. Pat. No. 5,766,213, issued to Hackman et al., Jun. 16, 1998. Hackman teaches the use of corrugated absorbent materials and body-gasketing longitudinal sides with accordion-like structures that can flex and deform. In the absorbent articles of the present invention, corrugated regions or extensible regions in the outer absorbent member can be useful in decoupling deformation of the crotch region of the absorbent article from deformation of the back portion in use, thus allowing the back portion of the absorbent article to deform with an inverted-V shape for fitting into the buttocks while permitting the crotch region to deform with a W-shape for fitting the vestibule of the user.

The article may also comprise hydrophobic material around the sides of the absorbent core to further reduce edge leakage. For example, hydrophobic fibers may be placed in discrete areas, such as around the periphery of the hydrophilic absorbent core, to provide barriers against leakage, as exemplified in U.S. Pat. No. 5,817,079, issued to R. Bergquist et al., Oct. 6, 1998. A related approach which can be applied to the present invention is given by Csillag in U.S. Pat. No. 4,015,604, issued Apr. 5, 1977. Likewise, Canadian Patent No. 884,608 issued to Levesque, Nov. 2, 1971, relates to treating the edges of a sanitary napkin product with hydrophobic material in order to prevent side leakage. In accordance with Levesque, the absorbent layer in the zone of the edges of the absorbent material is rendered hydrophobic while being maintained in a gas and moisture vapor permeable condition.

Optionally, a surge layer can be disposed between the topsheet and the absorbent core, specifically above the central absorbent section, to enhance intake of fluid, particularly urine and particularly in absorbent articles intended for urine management such as diapers, training pants, or incontinence pads. The surge layer is typically a non-absorbent or marginally absorbent (e.g., having an Intrinsic Absorbent Capacity less than about 0.9 and specifically less than about 0.3) high-loft nonwoven web, such as a bonded carded web, of synthetic materials such as polyethylene or polypropylene, which does not retain liquid but helps to distribute it into the underlying absorbent core. Basis weights for such a surge layer are desirably between about 15 gsm and about 100 gsm, with porosities (the fraction of volume not occupied by solid) above about 96%. Exemplary surge layers are described in U.S. Pat. No. 5,562,650, issued Oct. 8, 1996 to Everett et al. and U.S. Pat. No. 5,429,629, issued Jul. 4,1995 to Latimer.

Means can also be applied to reduce the tendency of a pad or sanitary napkin to bunch or fold over onto itself during transverse compression. Wings, flaps, or tabs extending from the absorbent article in the crotch region can fold over the edge of undergarments of the wearer to provide better fit, stability, and leakage protection, and can reduce undesirable bunching of the article. Wings and related structures are taught in the U.S. Pat. No. 5,267,992, "Shaped Sanitary Napkin with Flaps," issued to K. J. Van Tilburg, Dec. 7, 1993 and U.S. Pat. No. 4,285,343, "Sanitary Napkin," issued to R. M. McNair, Aug. 25, 1981. Elasticized leg cuffs may also be added, either along the longitudinal sides of the article, or adjacent the bending lines of an absorbent article of the present invention.

Apart from the use of wings and fasteners for stability and fit, preshaping of a pad can also be useful, including the means disclosed in U.S. Pat. No. 5,545,156, issued Aug. 13, 1996 to DiPalma et al. Thus, a pad can be contoured or shaped for better body fit. In one embodiment, the absorbent article is profiled so that it is thicker in the center of the article and tapers so it becomes thinner at the longitudinal sides and/or at the front and back edges. Profiling can be achieved by layering, by depositing absorbent material with a nonuniform basis weight distribution, by using profiled molds to shape the article, by selective calendering of the article, and so forth.

Bending Lines (Crease Lines and Shaping Lines)

Bending lines, including shaping lines and crease lines, can have a variety of geometrical forms. In one embodiment, the shaping line has a geometry similar to a double headed arrow with reverse arrow heads, or ">-<", centered along the longitudinal centerline of the article between the crease lines, and with the longitudinal axis of the arrow aligned with the longitudinal centerline (longitudinal axis) of the article. Such a geometry for the shaping line further helps the central region of the absorbent core between the outward "arrow heads" to deflect upward while downward deflection occurs along the crease lines. Another useful geometry for the shaping line in the upper absorbent member is a pair of outwardly concave arcuate lines whose midpoints touch or approach each other, longitudinally aligned and substantially symmetrically placed about both sides of the longitudinal centerline in the crotch region between the outer crease lines, and desirably smaller in length than the crease lines. Such arcuate shaping lines resemble the shape of a right and left parentheses placed back to back, or ")(", with the vertical axis of the parentheses substantially aligned with the longitudinal centerline of the article. Likewise, the shaping line in many embodiments can be described as convex toward the longitudinal centerline of the article and generally contained within the absorbent core and specifically generally contained within the central absorbent section.

Generally, the shaping line comprises a central longitudinal portion and outwardly spanning sections which traverse a substantial distance from the vicinity of the longitudinal centerline to the vicinity of the longitudinal edge of the central absorbent section. Similarly, the shaping line in several embodiments can comprise longitudinal components near the centerline and additional oblique components (oblique relative to the longitudinal centerline of the article).

The shaping line or crease lines of the absorbent article can generally be created in any way likely to guide the folding of a flexible material having a degree of intrinsic stiffness such as an air laid pad, a mat of fluff pulp, a stack of tissue layers, a web of coform material or other fiber-polymer composites, or a high-loft nonwoven web. The shaping line or crease lines desirably are produced by one of more treatment methods such as embossing, stamping, or other known methods for creating densified regions, as described in U.S. Pat. No. 4,655,759, issued Apr. 7, 1987 to A. Y. Romans-Hess et al. Other methods for line formation include slitting; cutting; notching; tearing; thermobonding (application of heat to create bonding, particularly with thermoplastic materials or heat-setting resins); hot pressing (simultaneous application of heat and pressure, especially in conjunction with thermoplastic binder materials, thermosetting plastics, or heat setting resins); local melting; ultrasonic bonding; perforating; perf-embossing; needling; impregnation by resins, waxes, or thermoplastics; hydraulic cutting by water jets or other fluid jets; pre-folding; creasing; scoring; or removing material by abrasion, ablation, picking, laser cutting, or suction.

In certain embodiments, then, the crease lines and optional shaping lines may be a series of perforations, notches, cuts, tears, or slits optionally having portions not fully perforated, notched, cut, torn, or slit along a line's length for increased integrity. Crease lines and shaping lines formed by slitting or creation of densified areas are believed to be especially useful due to their ease of application and general effectiveness.

Treatment methods for creating a shaping line or crease lines are applied to make a distinct line differing in material properties from the surrounding material in a manner that promotes folding at or near the treated line during lateral compression of the article. Material properties that may be modified to encourage folding can include density, stiffness, basis weight, tensile strength, chemical composition (e.g., resins and fibers versus fibers alone), and internal integrity or bond strength (especially z-direction bond strength). A line can be a gap or void space between absorbent members, wherein the line has a material property, for example, of zero basis weight relative to the surrounding non-zero basis weight regions.

METHODS OF MAKING

Generally, automated equipment can be used similar to the production lines already used for production of sanitary napkins, diapers, and the like, with minor modifications to produce the present invention. Modular systems are especially preferred, wherein the various unit operations in the production line can be moved and replaced with other modules without necessitating a complete rebuild of a machine.

The components of the absorbent articles of the present invention can be assembled and produced using any means known in the art. Examples of high-speed machines and control systems for production of absorbent articles are disclosed, by way of example only, in U.S. Pat. No. 5,235,515, issued to Ungpiyakul et al., Aug. 10, 1993; U.S. Pat. No. 5,817,394, issued to Alikhan et al., Oct. 6, 1998; and European Patent Application 873,274-A1, published Oct. 28, 1998.

The production line can include a hammermill for production of comminuted fibers, if fluff pulp is to be used, or absorbent material in roll form can be provided, including airlaid webs, coform, mechanically softened pulp sheets, tissue webs, and the like. Likewise, the nonwoven or film components of the absorbent article are also generally provided in roll form. Roll goods are unwound and cut to shape, using methods such as die cutting, slitters, or water jets, and the components placed in proper relationship one to another, typically with online bonding at selected regions provided by spray adhesive, contact with ultrasonic horns or heated embossing elements, or other bonding means known in the art. Components may be moved on continuous belts from one operation to another, and may be further transported with vacuum pick up shoes, jets of air, mechanical pincers, and the like.

For example, one or more webs of airlaid material, coform, densified fluff pulp, or a microstrained pulp sheet of width suitable for the absorbent core of an absorbent article may be unwound. A single roll of absorbent material could be slit into a wide strip for use as the lower absorbent member and a narrower strip for use as the unitary absorbent layer. The middle absorbent member desirably is provided from a separate source such as another roll of absorbent material, or encased pouches of free flowing absorbent material, or pledgets of fluff pulp cut to a desired shape and size. The lower absorbent member is provided with spaced apart substantially longitudinal crease lines by means of slitters, embossing rolls, mechanical stamping means, thermal or ultrasonic welders which densify the web along a crease line, mechanical folding devices or creasers, and the like. The lower absorbent member travels in the machine direction and is joined to a moving web of barrier material, such as an embossed polyethylene film, a resin-impregnated or sized tissue web, or an apertured film or impervious web with spaced apart openings therein and impervious side regions. The barrier material is unwound from a roll and is guided by guiding means rolls, turning bars, foils, channels, pneumatic jets, vacuum slots or shoes, or the like, to be above the lower absorbent member and come into contacting relationship therewith. A middle absorbent member such as a pouch of free flowing nits encased in a liquid pervious encasement, a pledget of fluff pulp, and the like, is prepared and joined to the wicking barrier at discrete intervals. An unitary absorbent layer, desirably also unwound from a roll of absorbent material, travels in the same direction with the lower absorbent member, the wicking barrier, and the middle absorbent member, and is joined thereto, desirably being cut to size and centrally placed over the middle absorbent member at discrete intervals to form an absorbent core with a horizontal wicking barrier.

The absorbent core is then sandwiched between a backsheet and a topsheet. An optional central rising member may also be disposed between the backsheet and the horizontal wicking barrier. Additional absorbent layers may be joined to the absorbent core.

The topsheet and backsheet can be cut together to define the proper shape for the article. Wings, adhesive tape strips, mechanical fasteners, cuffs, and the like may also be added using methods known in the art.

The upper absorbent member may be preshaped into a cup-like or convex shape prior to being superposed over the middle absorbent member. This may be achieved by a combination of heat and pressure applied to an airlaid web against a molded surface, or by cold calendering and the like. The upper absorbent member need not be provided in continuous form, but may be provided as discrete molded units wherein airlaid material or wet laid fibers are shaped and bonds are formed by heating or drying in the shaped form to preshape the member. The discrete units can then be conveyed by known means and then registered with the middle absorbent member as it moves and joined therewith, prior to addition of the topsheet to the absorbent core.

EXAMPLES

Examples of absorbent articles were made with the materials listed in Table 1 below:

TABLE 1

Basic materials used in construction of absorbent articles for the Examples.

| Component | Manufacturer | Description |
|---|---|---|
| Topsheet | | |
| Spunbond material | Kimberly-Clark Corp. | 0.6 osy polypropylene spunbond web, "Delta" version, treated with 0.3% add-on of surfactant (described below), pin apertured |
| Surfactant treatment | ICI Americas, Inc. | 45% (w) polyethoxlated hydrogenated ethoxylated castor oil; 55% (w) sorbitan monooleate |
| Adhesive | National Starch and Chemical Co. | NS-34-5610: slot-coated, pinstripe pattern, applied at a level of about 5 gsm or less. |
| Fluff | Kimberly-Clark Corp. | Coosa River CR54 debonded softwood pulp comminuted with a hammermill |
| Densified airlaid webs | | |
| Completed web | Concert Fabrication, Ltee | 90% softwood fibers and 10% binder fibers with overall densities of 0.1–0.2 g/cc. |
| Fibers | Weyerhaeuser Co. | NB-416: bleached southern softwood kraft |
| Binder fibers | Hoechst Celanese Corp. (Trevira Company) | Celbond #255: PET core, activated co-polyethylene sheath, 50/50 core/sheath ratio, concentric, 2.8 dpf, with T-255 fiber finish |
| Coform | Kimberly-Clark Corp. | 70% bleached kraft southern softwood, 30% polyethylene, basis weight of 228 gsm |
| Impervious wicking barrier | | |
| Polyolefin film, white | Edison Plastics Co. | A low density polyethylene, 18 gsm, opaque with added white pigment, about 1 mil |
| Pervious wicking barrier | | |
| Spunbond web | Kimberly-Clark Corp | 0.8 osy 2.7 denier, rose color, no surfactant |
| Backsheet | | |
| Polyolefin film | Edison Plastics Co. | A low density polyethylene, 20 gsm, rose color, 2 mil gauge after embossed with pattern MFST (male fine square taffeta), coated with contact adhesive on one side |
| Adhesive | National Starch and Chemical Co. | NS-34-5610, less than 15 gsm added, slot-coated, pinstripe pattern |
| Garment adhesive | National Starch and Chemical Co. | NS-34-5602, less than 45 gsm applied, slot coated, two 15 mm side lines of adhesive with a 19 mm space between them |
| Release paper | Akrosil Inc. | White base sheet, one side coated with silicone release agent, other side printed |

Examples were made generally according to FIGS. 1 and 2, with exceptions noted below, and with the materials described in Table 1 unless otherwise noted.

In Example 1, the backsheet was cut to a dogbone shape 84 mm wide and 238 mm long. The lower absorbent member was layer of a about 200 gsm (grams per square meter) fluff pulp with a density of about 0.1 g/cc, cut in a rounded rectangular shape 72 mm wide and 226 mm long, adhesively attached to the backsheet and centered thereon. Superposed on the lower absorbent member was either an impervious wicking barrier or pervious wicking barrier, in various embodiments, cut to the same size as the backsheet and adhesively attached thereto. Superposed on the wicking barrier was a middle absorbent member consisting of a 656 gsm pledget of fluff pulp having a density of 0.14 g/cc, unembossed, cut to an oval shape 82 mm long and 38 mm wide. The upper absorbent member was coform with a basis weight of 228 gsm cut to an ellipse 46 mm wide and 212 mm long. A topsheet cut to the same size as the backsheet was adhesively attached to the upper absorbent member and the exposed wicking barrier. The topsheet was connected to the backsheet by virtue of adhesive attachment to both sides of the horizontal wicking barrier. The garment side of the backsheet was provided with two longitudinal adhesive strips 190 mm long and 15 mm wide, centered about the longitudinal centerline and spaced apart about 10 mm. The longitudinal ends of the backsheet were further provided with transverse strips of adhesive 15 long and 100 mm wide centered on the lobe portion of the dogbone pattern. Release paper was provided over the adhesive material.

In Example 2, the oval pledget was replaced with an "e"-folded section of densified airlaid web with a basis weight of 175 gsm and a density of 0.1 g/cc, cut to dimensions of 110 mm by 70 mm and folded with two creases normal to the long direction and evenly spaced apart to yield an "e"-folded web with a width of about 40 mm and a length of 70 mm. The creases defining the folds were oriented in the longitudinal direction of the article so that the e-fold shape of the central rising member would be evidenced in a transverse cross-section, as shown in FIG. 3.

It will be appreciated that the foregoing examples, given for purposes of illustration, are not to be construed as limiting the scope of this invention. Although only a few exemplary embodiments of this invention have been described in detail above, those skilled in the art will readily appreciate that many modifications are possible in the exemplary embodiments without materially departing from the novel teachings and advantages of this invention. Accordingly, all such modifications are intended to be included within the scope of this invention, which is defined in the following claims and all equivalents thereto. Further, it is recognized that many embodiments may be conceived that do not achieve all of the advantages of some embodiments, particularly of the preferred embodiments, yet the absence of a particular advantage shall not be construed to necessarily mean that such an embodiment is outside the scope of the present invention.

We claim:

1. An absorbent article, the absorbent article having a longitudinal centerline, a transverse centerline, two longitudinal sides, a target zone and a body side, the absorbent article comprising:
   a) a liquid impervious backsheet;
   b) a liquid pervious topsheet attached to the backsheet;
   c) a lower absorbent member disposed above the backsheet, the lower absorbent member comprising a pair of spaced apart, substantially longitudinal crease lines in the target zone disposed on opposite sides of the longitudinal centerline of the article, the pair of crease lines having a distance therebetween;
   d) a horizontal wicking barrier having a width and disposed above the lower absorbent member;
   e) a middle absorbent member having a lateral width substantially less than the distance between the crease lines in the target zone, the middle absorbent member being disposed above the horizontal wicking barrier; and
   f) an upper absorbent member having longitudinal sides and a width in the target zone greater than the width of the middle absorbent member and less than the width of the horizontal wicking barrier, disposed above the middle absorbent member and beneath the topsheet,
   wherein the middle absorbent member is at least in part adjacently disposed above the horizontal wicking barrier.

2. The absorbent article of claim 1, wherein the width of the upper absorbent member in the target zone is no greater than distance between crease lines in the lower absorbent member.

3. The absorbent article of claim 1, wherein the middle absorbent member has a thickness of about 2 mm or greater, a width in the target zone between about 20 mm and about 40 mm, and a length between about 25 mm and 70 mm.

4. The absorbent article of claim 1, wherein the crease lines are embossments.

5. The absorbent article of claim 1, wherein the crease lines are scoremarks.

6. The absorbent article of claim 1, wherein the crease lines are selected from cuts, slits, perforations, and notches.

7. The absorbent article of claim 1, wherein the crease lines extend longitudinally for a length of about 30 mm or greater.

8. The absorbent article of claim 1, wherein the middle absorbent member has a length and the upper absorbent member has a longitudinal length greater than the length of the middle absorbent member.

9. The absorbent article of claim 1, further comprising a central rising member.

10. The absorbent article of claim 9, wherein the central rising member comprises an absorbent web.

11. The absorbent article of claim 1, wherein the middle absorbent member comprises a central rising member.

12. The absorbent article of claim 11, wherein the central rising member prior to lateral compression has a thickness of about 5 mm or less.

13. The absorbent article of claim 1, wherein the wicking barrier is liquid impervious.

14. The absorbent article of claim 1, wherein the wicking barrier is liquid pervious.

15. The absorbent article of claim 1, wherein the wicking barrier is a polymeric film.

16. The absorbent article of claim 1, wherein the wicking barrier is selected from a spunbond web and a meltblown web.

17. The absorbent article of claim 1, wherein the wicking barrier comprises a cellulosic web treated with hydrophobic agents.

18. The absorbent article of claim 1, wherein the middle absorbent member comprises a web folded upon itself to have a thickness of at least three layers of the web.

19. The absorbent article of claim 1, wherein the middle absorbent member comprises a section of a resilient material folded to have a cross-section substantially in a letter "e" shape.

20. The absorbent article of claim 1, wherein the middle absorbent member has an absorbent capacity of about 3 ml of fluid or greater.

21. The absorbent article of claim 1, wherein the middle absorbent member has an absorbent capacity of about 10 ml of fluid or greater.

22. The absorbent article of claim 1, wherein the middle absorbent member comprises a fibrous web selected from an airlaid cellulosic web and a mat of fluff pulp.

23. The absorbent article of claim 1, wherein the lower absorbent member and the middle absorbent member each have a thickness and the thickness of the lower absorbent member is substantially less than the thickness of the middle absorbent member.

24. The absorbent article of claim 1, wherein the middle absorbent member has a thickness that increases substantially when wetted.

25. The absorbent article of claim 1, wherein the horizontal wicking barrier comprises a plurality of webs or films.

26. The absorbent article of claim 1, wherein the middle absorbent member has a Wet Bulk of about 6 cc/g or greater.

27. The absorbent article of claim 1, wherein the middle absorbent member has a Wet Bulk of about 10 cc/g or greater.

28. The absorbent article of claim 1, wherein the upper absorbent member further comprises one of a foam, a foam-fiber composite, and a foam-structured fibrous absorbent material.

29. An absorbent article having a target zone, a longitudinal direction, a transverse direction, a vertical direction substantially normal to both the longitudinal and transverse directions, and a body side, the absorbent article comprising;
   a) a liquid impervious backsheet;
   b) a lower absorbent member disposed above the backsheet;
   c) a horizontal wicking barrier disposed over the lower absorbent member, the wicking barrier having a width in the target zone;
   d) a middle absorbent member disposed above the wicking barrier and having a maximum width in the target zone;
   e) an upper absorbent member disposed above the middle absorbent member having a width in the target zone no less than the maximum width of the middle absorbent member in the target zone, the upper absorbent member being predisposed to deflect upward during laterally inward compression of the absorbent article; and
   f) a topsheet connected to the backsheet,
   wherein the middle absorbent member is at least in part adjacently disposed above the horizontal wicking barrier.

30. The absorbent article of claim 29, wherein the middle absorbent member comprises cellulosic fibers reinforced with thermoplastic material.

31. The absorbent article of claim 29, wherein the middle absorbent member comprises cellulosic fibers having a wet:dry tensile strength ratio of at least 0.1.

32. The absorbent article of claim 29, wherein the middle absorbent member has a Wet Bulk of about 6 cc/g or greater.

33. The absorbent article of claim 29, wherein the middle absorbent member has a Wet Bulk of about 10 cc/g or greater.

34. The absorbent article of claim 29, wherein the upper absorbent member further comprises one of a foam, a foam-fiber composite, and a foam-structured fibrous absorbent material.

35. An absorbent article having a target zone, a longitudinal direction, a transverse direction, a vertical direction substantially normal to both the longitudinal and transverse directions, and a body side, the absorbent article comprising:
   a) a liquid impervious backsheet;
   b) a lower absorbent member disposed above the backsheet;
   c) a horizontal wicking barrier disposed over the lower absorbent member, the wicking barrier having a width in the target zone;
   d) a middle absorbent member disposed above the wicking barrier and having a maximum width in the target zone;
   e) an upper absorbent member disposed above the middle absorbent member having a width in the target zone no less than the maximum width of the middle absorbent member in the target zone, the upper absorbent member being predisposed to deflect upward during laterally inward compression of the absorbent article; and
   f) a topsheet connected to the backsheet,
   wherein the lower absorbent member comprises pair of spaced apart crease lines extending in the longitudinal direction.

36. An absorbent article having a target zone, a longitudinal direction, a transverse direction, a vertical direction substantially normal to both the longitudinal and transverse directions, and a body side, the absorbent article comprising:
   a) a liquid impervious backsheet;
   b) a lower absorbent member disposed above the backsheet;
   c) a horizontal wicking barrier disposed over the lower absorbent member, the wicking barrier having a width in the target zone;
   d) a middle absorbent member disposed above the wicking barrier and having a maximum width in the target zone;
   e) an upper absorbent member disposed above the middle absorbent member having a width in the target tone no less than the maximum width of the middle absorbent member in the target zone, the upper absorbent member being predisposed to deflect upward during laterally inward compression of the absorbent article; and
   f) a topsheet connected to the backsheet,
   wherein the horizontal wicking barrier comprises a pair of spaced apart longitudinal upward projections with a distance therebetween equal to or greater than the width of the upper absorbent member in the target zone, the longitudinal upward projections being adapted to engage the longitudinal sides of the upper absorbent member when the article is compressed laterally inward in the target zone and
   wherein the lower absorbent member is contiguous in the target zone.

37. A method for producing an absorbent article having a longitudinal centerline and a transverse centerline substantially normal to the longitudinal centerline comprising:
   a) providing a backsheet;
   b) disposing a substantially planar lower absorbent member above the backsheet, the lower absorbent member having a width along the transverse centerline of the article and comprising longitudinal crease lines therein;
   c) disposing a horizontal wicking barrier over the lower absorbent member;
   d) disposing a middle absorbent member over the horizontal wicking barrier, the middle absorbent member being substantially centered about the longitudinal centerline of the article and having a width substantially less than the width of the lower absorbent member along the transverse centerline of the article;
   e) disposing an upper absorbent member over the middle absorbent member, the upper absorbent member having a width along the transverse centerline of the article greater than the width of the middle absorbent member;
   f) disposing a topsheet above the upper absorbent member and the lower absorbent member; and
   g) securing the topsheet to the backsheet,
   wherein the middle absorbent member is at least in part adjacently disposed over the horizontal wicking barrier.

* * * * *